United States Patent

Schieweck et al.

(10) Patent No.: US 7,317,015 B2
(45) Date of Patent: Jan. 8, 2008

(54) 2-SUBSTITUTED PYRIMIDINES

(75) Inventors: Frank Schieweck, Hessheim (DE); Jordi Tormo i Blasco, Laudenbach (DE); Carsten Blettner, Mannheim (DE); Bernd Müller, Frankenthal (DE); Markus Gewehr, Kastellaun (DE); Wassilios Grammenos, Ludwigshafen (DE); Thomas Grote, Wachenheim (DE); Andreas Gypser, Mannheim (DE); Joachim Rheinheimer, Ludwigshafen (DE); Peter Schäfer, Ottersheim (DE); Anja Schwögler, Mannheim (DE); Oliver Wagner, Neustadt (DE); Siegfried Strathmann, Limburgerhof (DE); Ulrich Schöfl, Brühl (DE); Maria Scherer, Godramstein (DE); Reinhard Stierl, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/565,656

(22) PCT Filed: Jul. 3, 2004

(86) PCT No.: PCT/EP2004/007258

§ 371 (c)(1),
(2), (4) Date: Jun. 26, 2006

(87) PCT Pub. No.: WO2005/019187

PCT Pub. Date: Mar. 3, 2005

(65) Prior Publication Data

US 2007/0129380 A1    Jun. 7, 2007

(30) Foreign Application Priority Data

Jul. 24, 2003 (DE) ................. 103 33 857

(51) Int. Cl.
A01N 43/54 (2006.01)
C07D 239/42 (2006.01)
C07D 401/04 (2006.01)
C07D 239/02 (2006.01)

(52) U.S. Cl. .................... 514/256; 544/325

(58) Field of Classification Search ............ None
See application file for complete search history.

(56) References Cited

U.S. PATENT DOCUMENTS

2004/0116429 A1    6/2004 Grote et al.

FOREIGN PATENT DOCUMENTS

| CA | 2 467 683 A1 | 5/2003 |
|---|---|---|
| CA | 2467683 A1 | 5/2003 |
| CA | 2 467 683 * | 5/2004 |
| WO | WO-02/074753 A | 9/2002 |
| WO | WO-03/043993 A | 5/2003 |

* cited by examiner

*Primary Examiner*—James O. Wilson
*Assistant Examiner*—Erich Leeser
(74) *Attorney, Agent, or Firm*—Birch, Stewart, Kolasch & Birch, LLP

(57) ABSTRACT

The invention relates to 2-substituted pyrimidines of the formula I

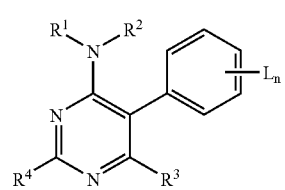

in which the index n and these substituents $R^1$, $R^2$ and $R^3$ are as defined in the description and $R^4$ is as defined below:
$R^4$ corresponds to one of the formulae

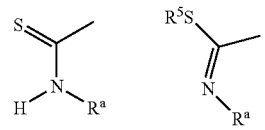

where
$R^a$ is hydrogen, $C_1$-$C_6$-alkyl, $C_2$-$C_8$-alkenyl, $C_2$-$C_8$-alkynyl, $C_3$-$C_6$-cycloalkyl or $C_1$-$C_4$-alkoxy and
$R^5$ is hydrogen, $C_1$-$C_6$-alkyl, $C_2$-$C_6$-alkenyl, $C_2$-$C_6$-alkynyl, $C_1$-$C_4$-alkyloxy-$C_1$-$C_2$-alkyl, phenyl-$C_1$-$C_2$-alkyl or phenyloxy-$C_1$-$C_2$-alkyl,
to processes for preparing these compounds, to compositions comprising these compounds and to their use as pesticides.

11 Claims, No Drawings

2-SUBSTITUTED PYRIMIDINES

The invention relates to 2-substituted pyrimidines of the formula I

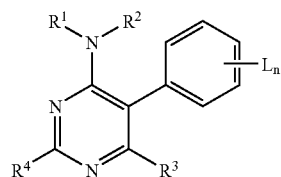

in which the index and the substituents are as defined below:

n is an integer from 1 to 5;

L is halogen, cyano, cyanato (OCN), $C_1$-$C_8$-alkyl, $C_2$-$C_8$-alkenyl, $C_2$-$C_8$-alkynyl, $C_1$-$C_6$-alkoxy, $C_2$-$C_8$-alkenyloxy, $C_2$-$C_8$-alkynyloxy, $C_3$-$C_6$-cycloalkyl, $C_4$-$C_6$-cycloalkenyl, $C_3$-$C_6$-cycloalkyloxy, $C_4$-$C_6$-cycloalkenyloxy, nitro, —C(=O)-A, —C(=O)—O-A, -C(=O)—N(A')A, C(A')(=N—OA), N(A')A, N(A')-C(=O)-A, N(A")—C(=O)—N(A')A, S(=O)$_m$-A, S(=O)$_m$—O-A or S(=O)$_m$—N(A')A, m is 0, 1 or 2;

A, A', A" independently of one another are hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, phenyl, where the organic radicals may be partially or fully halogenated or may be substituted by nitro, cyanato, cyano or $C_1$-$C_4$-alkoxy; or A and A' together with the atoms to which they are attached are a five- or six-membered saturated, partially unsaturated or aromatic hetero cycle which contains one to four heteroatoms from the group consisting of O, N and S;

where the aliphatic groups of the radical definitions of L for their part may be partially or fully halogenated or may carry one to four groups $R^u$:

$R^u$ is cyano, $C_1$-$C_6$-alkoxy, $C_3$-$C_6$cycloalkyl, $C_2$-$C_8$-alkenyloxy, $C_2$-$C_8$-alkynyloxy, $C_4$-$C_6$-cycloalkenyl, $C_3$-$C_6$-cycloalkyloxy, $C_4$-$C_6$-cycloalkenyloxy, —C(=O)-A, —C(=O)—O-A, —C(=O)—N(A')A, C(A')(=N—OA), N(A')A, N(A')-C(=O)-A, N(A")-C(=O)—N(A')A, S(=O)$_m$-A, $R^1$, $R^2$ independently of one another are $C_1$-$C_6$-alkyl, $C_2$-$C_6$-alkenyl, $C_2$-$C_6$-alkynyl, $C_3$-$C_6$-cycloalkyl, $C_3$-$C_6$-halocycloalkyl, where the aliphatic groups of the radical definitions of $R^1$ and $R^2$ may for their part be partially or fully halogenated or may carry one to four groups $R^v$:

$R^v$ is cyano, $C_3$-$C_6$-cycloalkyl, $C_4$-$C_6$-cycloalkenyl, hydroxyl, $C_1$-$C_6$-alkoxy, $C_2$-$C_8$-alkenyloxy, $C_2$-$C_8$-alkynyloxy, $C_3$-$C_6$-cycloalkyloxy, $C_4$-$C_6$-cycloalkenyloxy, $C_1$-$C_6$-alkylthio, —C(=O)-A, —C(=O)—O-A, —C(=O)—N(A')A, C(A')(=N—OA), N(A')A, N(A')-C(=O)-A, N(A")-C(=O)—N(A')A, S(=O)$_m$-A, S(=O)$_m$—O-A or S(=O)$_m$—N(A')A or phenyl, where the phenyl moiety may carry one to three radicals selected from the group consisting of halogen, $C_1$-$C_6$-alkyl, $C_2$-$C_6$-alkenyl, $C_2$-$C_6$-alkynyl, $C_3$-$C_6$-cycloalkyl, $C_1$-$C_6$-halogenalkyl, $C_1$-$C_6$-alkoxy, cyano, nitro, —C(=O)-A, —C(=O)—O-A, —C(=O)—N(A')A, C(A')(=N—OA), N(A')A;

$R^2$ may additionally be hydrogen;

$R^1$ and $R^2$ may also, together with the nitrogen atom to which they are attached, form a saturated or unsaturated five- or six-membered ring which may be interrupted by an ether (—O—), carbonyl (C=O—), thio (—S—), sulfoxyl (—S[=O]—) or sulfenyl (—SO$_2$—) or a further amino —(—N($R^a$)— group where $R^a$ is hydrogen or $C_1$-$C_6$-alkyl and/or may contain one or more substituents from the group consisting of halogen, $C_1$-$C_6$-alkyl, $C_1$-$C_6$-haloalkyl and oxy-$C_1$-$C_3$-alkylenoxy;

$R^3$ is halogen, cyano, $C_1$-$C_4$-alkyl, $C_2$-$C_4$-alkenyl, $C_2$-$C_4$-alkynyl, $C_3$-$C_6$cycloalkyl, $C_1$-$C_4$-alkoxy, $C_3$-$C_4$-alkenyloxy, $C_3$-$C_4$-alkynyloxy, $C_1$$C_6$-alkylthio, di-($C_1$-$C_6$-alkyl)amino or $C_1$-$C_6$-alkylamino, where the alkyl, alkenyl and alkynyl radicals of $R^3$ may be substituted by halogen, cyano, nitro, $C_1$-$C_2$-alkoxy or $C_1$-$C_4$-alkoxycarbonyl;

$R^4$ corresponds to one of the formulae

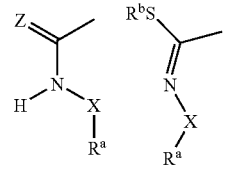

where

X is a direct bond, —(C=O)—, —(C=O)—NH, —(C=O)—O—, —O—, —NR$^c$—, where the molecule moiety to the left in each case is attached to the nitrogen atom;

$R^a$ is hydrogen, methyl, benzyl, trofluoromethyl, allyl, propargyl or methoxymethyl;

$R^b$ is hydrogen, $C_1$-$C_6$-alkyl, $C_2$-$C_6$-alkynyl;

$R^c$ is hydrogen, methyl or $C_1$-$C_4$acyl and

Z is S or NR$^b$;

where the aliphatic groups of the radical definitions of $R^a$, $R^b$ and/or $R^c$ for their part may carry one or two groups $R^w$:

$R^w$ is halogen, OR$^x$, NHR$^x$, $C_1$-$C_6$-alkyl, $C_1$-$C_4$-alkoxycarbonyl, $C_1$-$C_4$-acylamino, [1,3]dioxolane-$C_1$-$C_4$-alkyl, [1,3]dioxane-$C_1$-$C_4$-alkyl, where $R^x$ is hydrogen, methyl, allyl or propargyl.

Moreover, the invention relates to a process for preparing these compounds, to compositions comprising them and to their use for controlling phytopathogenic harmful fungi.

Fungicidal pyrimidines carrying a cyanamino substituent in the 2-position are known from WO-A 01/96314. Furthermore, fungicidal pyrimidines carrying, inter alia, an amide radical in the 2-position are known from WO-A 03/43993.

However, in many cases the activity of the abovementioned pyrimidines is unsatisfactory.

It is an object of the present invention to provide compounds having improved activity.

We have found that this object is achieved by the pyrimidines of the formula I defined at the outset. Moreover, we have found processes for their preparation and compositions comprising them for controlling harmful fungi.

The compounds I can be obtained by different routes.

It is possible, for example, to use sulfones of the formula II whose preparation is described in detail in WO-A 02/074753 or DE 10156279.9 and where R' is an unsubstituted or substituted $C_1$-$C_6$-alkyl radical or an unsubstituted or substituted phenyl radical as starting materials. Reaction of the sulfones II with metal cyanides III (Me⁺CN⁻) yields the nitrites IV. Metal cyanides are to be understood as meaning primarily alkali metal cyanides or alkaline earth metal cyanides or else covalent cyanides, such as tin tetracyanides.

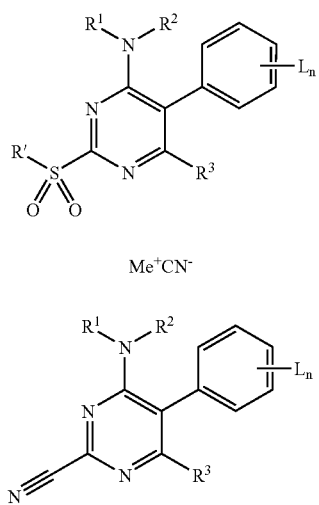

The exchange of the sulfonate group for the nitrile group is carried out by methods known from the literature, as described, for example, in WO-A 03/043993.

The further synthesis can be carried out as shown in Scheme 1:

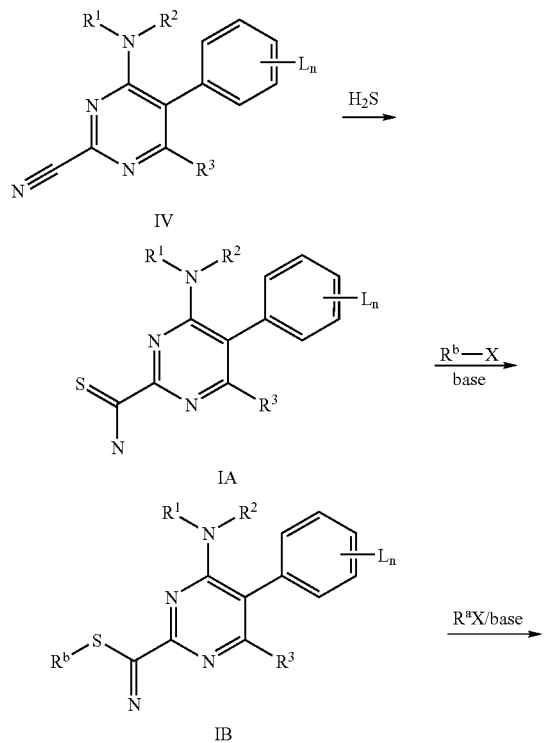

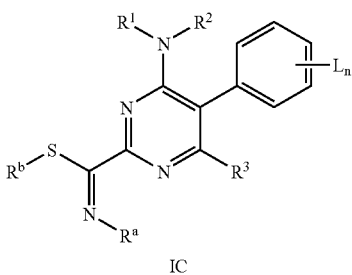

Using hydrogen sulfide, preferably under acidic conditions, the nitrile compound IV can be thiolyzed to give thioamide IA. The thiolysis is carried out under the conditions of the Pinner reaction (see Preparation Examples). Alkylation with $R^b$—X, where $R^b$ is as defined above and X is a leaving group, such as halide, sulfate or sulfonate, affords compounds of type IB. A further alkylation step with $R^a$—X, where $R^a$ is, for example, $C_1$-$C_6$-alkyl and X is a leaving group, such as halide, sulfate or sulfonate, yields compounds of type IC. The two alkylations mentioned above can also be carried out using Meerwein salts of the formula $(R^b)_3OBF_4$, analogously to the procedures given in Synth. Commun. 13, (1983), 753 or Helv. Chim. Acta 69, (1986), 1224.

Compounds IC' according to the invention in which $R^a$ is a $C_1$-$C_6$-alkoxy substituent can be obtained as shown in Scheme 2.

Scheme 2:

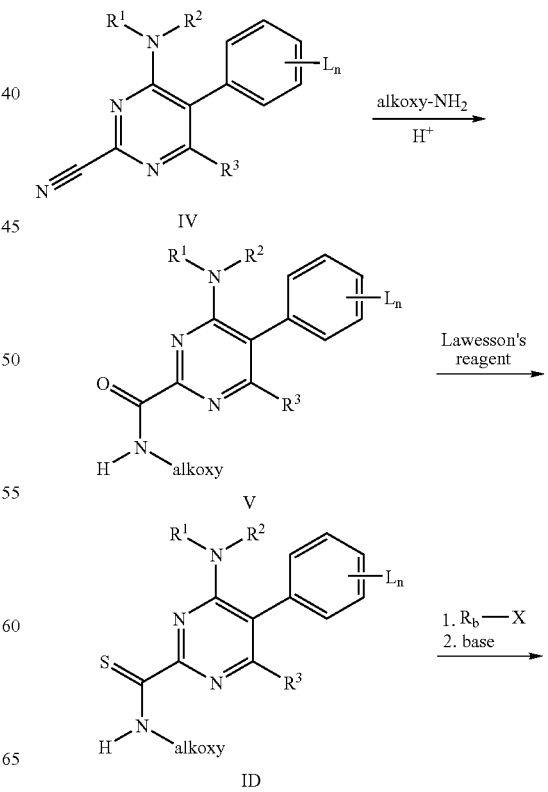

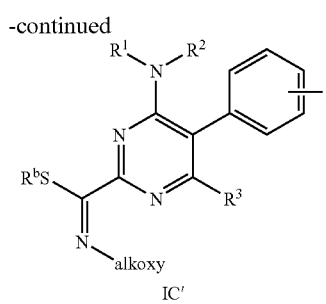

Starting with nitrile IV and using a $C_1$-$C_6$-alkoxyamine, the hydroxamic acid derivative V is obtained under acidic conditions. Conversion into the thione compound ID can be realized using, for example, phosphorus pentasulfide or Lawesson's reagent. Compounds IC according to the invention can be obtained by alkylation with $R^b$—X, where $R^b$ is as defined above and X is a leaving group, such as halide, sulfonate or sulfate.

An alternative synthesis of the compounds IC' and ID according to the invention is shown in Scheme 3.

In the synthesis, shown in Scheme 3, of compounds IC' and ID, the starting material used is the ester of the formula VIII. Reaction of VIII with hydroxylamines to give hydroxamic acids V can be carried out as described in Org. Lett. 3 (2001), 1053-56 or in J. Org. Chem. 85 (2000), 8415-20. The subsequent sulfurization can be carried out analogously to Aust. J. Chem. 41 (1988), 37. The iminohalides of the formula IX where Hal is halogen and in particular chlorine and bromine can be obtained analogously to Synthesis 9 (1991), 750-752. In an Appel reaction using, for example, carbon tetrabromide and triphenylphosphine, the corresponding bromine compounds are prepared. The latter can finally be reacted with mercaptans of the formula $R^b$SH and bases to give the compounds IC' according to the invention.

The radical $R^3$ (in particular alkyl) in the 6-position on the pyrimidine ring can be introduced by reaction with transition metal catalysis, such as Ni or Pd catalysis. In some cases it may be advisable to change the order and to introduce substituent $R^3$ first and then substituent $NR^1R^2$.

Scheme 3:

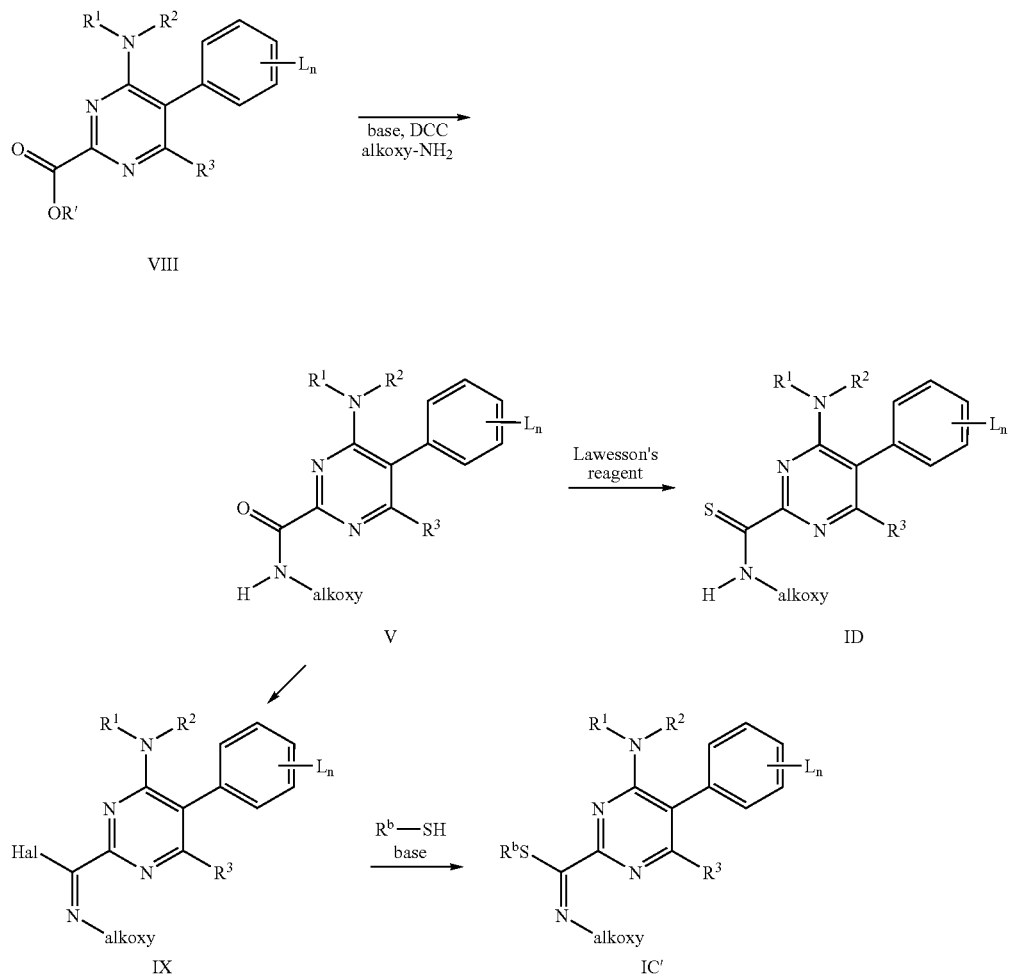

Scheme 4:

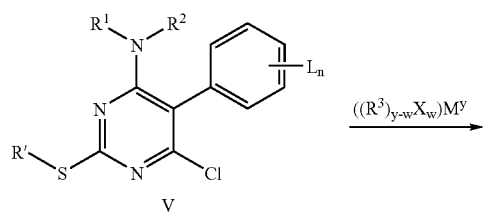

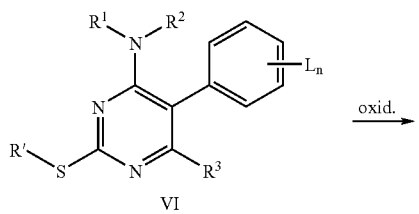

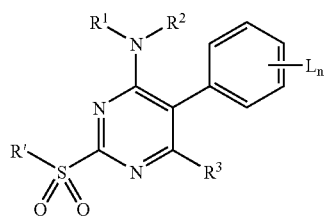

In the formula $(R^3)_{y-w}X_w\text{-}M^y$, M is a metal ion of valency Y, such as, for example, B, Zn, Mg, Cu or Sn, X chlorine, bromine, iodine or hydroxy, $R^3$ is preferably $C_1$-$C_4$-alkyl and w is a number from 0 to 3. This reaction can be carried out, for example, analogously to the following methods: J. Chem. Soc., Perkin Trans. 1 (1994), 1187, ibid. 1 (1996), 2345; WO-A 99/41255; Aust. J. Chem. 43 (1990); 733; J. Org. Chem. 43 (1978), 358; J. Chem. Soc., Chem. Commun. (1979), 866; Tetrahedron Lett. 34 (1993), 8267; ibid. 33 (1992), 413. In the formulae mentioned above, R' is in particular unsubstituted or substituted $C_1$-$C_6$-alkyl or unsubstituted or substituted phenyl.

Pyrimidines which carry a radical $R^4$ in the 2-position:

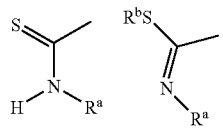

where $R^a$ is alkyl, alkenyl, alkynyl or cycloalkyl can also be prepared, for example, by the synthesis routes below.

Scheme 5:

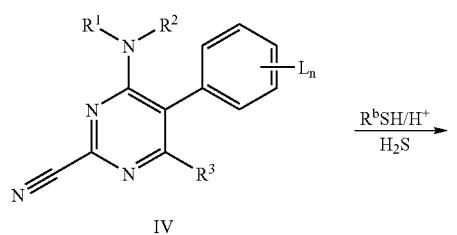

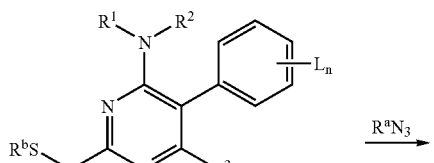

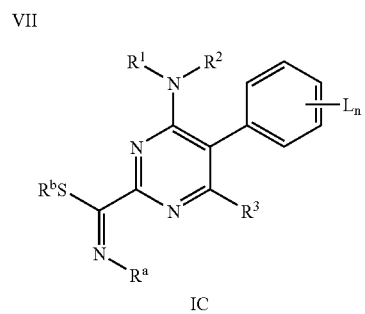

As shown in Scheme 5, the nitriles IV described above can be reacted under acidic conditions with mercaptans $R^b$SH, where $R^b$ is as defined above (see Chem. Ber. 113 (1980), 1898). In a subsequent reaction with azides, it is possible to introduce the radical $R^a$—N, where $R^a$ is as defined above (see Pol. J. Chem. 75 (2001), 975-82).

Scheme 6:

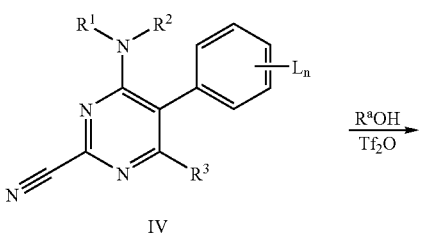

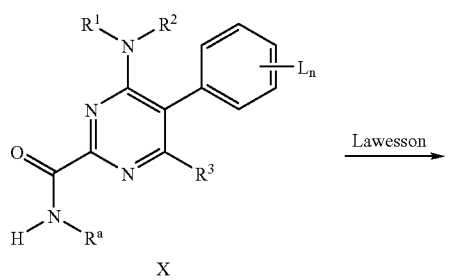

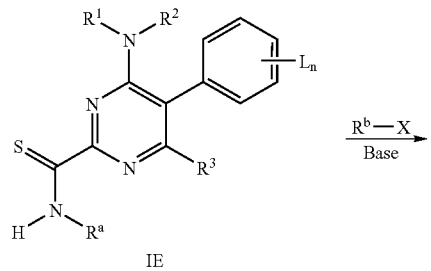

-continued $$\underset{IC}{\overset{R^1\diagdown N\diagup R^2}{\underset{R^bS}{\overbrace{\phantom{XXXX}}}\diagdown\diagup\overbrace{\phantom{XXXX}}\diagdown L_n}}$$

Scheme 6 shows an alternative synthesis route to the compounds IC according to the invention. Starting with the nitriles of the formula IV, the amides of the formula X are obtained in a modified Ritter reaction using alcohols of the formula $R^a$—OH and trifluoroacetic anhydride (see Tetrahedron Lett. 30 (1989), 581-82). The sulfurization with Lawesson's reagent can be carried out using the method described in J. Labelled Compd. Rad. 25 (1988), 335-343. The alkylation with $R^b$—X finally is carried out according to customary methods known from the literature, as described, for example, in Heterocycles 23 (1985), 2213-15.

What was said above refers in particular to the preparation of compounds in which $R^3$ is an alkyl group. If $R^3$ is a cyano group or an alkoxy substituent, the radical $R^3$ can be introduced by reaction with alkali metal cyanides and alkali metal alkoxides, respectively.

In the definitions of the symbols given in the formulae above, collective terms were used which are generally representative for the following substituents:

halogen: fluorine, chlorine, bromine and iodine;
alkyl: saturated straight-chain or branched hydrocarbon radicals having 1 to 4, 6 or 8 carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;
haloalkyl: straight-chain or branched alkyl groups having 1 to 8 carbon atoms (as mentioned above), where in these groups some or all of the hydrogen atoms may be replaced by halogen atoms as mentioned above, for example $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl;
alkenyl: unsaturated straight-chain or branched hydrocarbon radicals having 2 to 4 or 8 carbon atoms and a double bond in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;
alkadienyl: unsaturated straight-chain or branched hydrocarbon radicals having 4, 6 or 8 carbon atoms and two double bonds in any position;
haloalkenyl: unsaturated straight-chain or branched hydrocarbon radicals having 2 to 6 carbon atoms and a double bond in any position (as mentioned above), where in these groups some or all of the hydrogen atoms may be replaced by halogen atoms as mentioned above, in particular by fluorine, chlorine and bromine;
alkynyl: straight-chain or branched hydrocarbon groups having 2 to 6 carbon atoms and a triple bond in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;
cycloalkyl: mono- or bicyclic saturated hydrocarbon groups having 3 to 6 carbon ring members, for example $C_3$-$C_6$-cycloalkyl such as cyclopropyl, cyclobutyl, cyclopentyl, cyclohexyl;
five- or six-membered saturated, partially unsaturated or aromatic heterocycle which contains one to four heteroatoms from the group consisting of O, N and S:
5- or 6-membered heterocyclyl which contains one to three nitrogen atoms and/or one oxygen or sulfur atom or one or two oxygen and/or sulfur atoms, for example 2-tetrahydrofuryl, 3-tetrahydrofuryl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazo-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

- 5-membered heteroaryl which contains one to four nitrogen atoms or one to three nitrogen atoms and one sulfur or oxygen atom: 5-membered heteroaryl groups which, in addition to carbon atoms, may contain one to four nitrogen atoms or one to three nitrogen atoms and one sulfur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;
- 6-membered heteroaryl which contains one to three or one to four nitrogen atoms: 6-membered heteroaryl groups which, in addition to carbon atoms, may contain one to three and one to four nitrogen atoms, respectively, as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

The scope of the present invention includes the (R) and (S) isomers and the racemates of compounds of the formula I having chiral centers.

Hereinbelow, the embodiments of the invention are described in more detail.

With a view to the intended use of the pyrimidines of the formula I, particular preference is given to the following meanings of the substituents, in each case on their own or in combination:

Preference is given to compounds I in which $R^1$ is $C_1$-$C_6$-alkyl, $C_1$-$C_6$-haloalkyl, $C_2$-$C_6$-alkenyl, $C_2$-$C_6$-alkynyl or $C_3$-$C_6$-cycloalkyl and $R^2$ is hydrogen.

Especially preferred are compounds I in which $R^1$ is $C_1$-$C_6$-alkyl, $C_2$-$C_6$-alkenyl or $C_1$-$C_6$-haloalkyl branched in the α-position.

In addition, preference is given to compounds I in which $R^1$ is $C_1$-$C_4$-haloalkyl and $R^2$ is hydrogen.

Moreover, preference is given to compounds I in which $R^1$ and $R^2$ together with the nitrogen to which they are attached form a five- or six-membered ring which may be interrupted by an oxygen atom and may carry one or two $C_1$-$C_6$-alkyl substituents.

Especially preferred are groups $NR^1R^2$ such as—in particular in the α-position—methylated pyrrolidines or piperidines. 4-Methylpiperidine is furthermore preferred.

Moreover, particular preference is given to pyrimidines I in which the index n and the substituents $L^1$ to $L^5$ are as defined below:

n is 1 to 3;

L is halogen, cyano, $C_1$-$C_8$-alkyl, $C_2$-$C_{10}$-alkenyl, $C_2$-$C_{10}$-alkynyl, $C_1$-$C_6$-alkoxy, $C_2$-$C_{10}$-alkenyloxy, $C_2$-$C_{10}$-alkynyloxy, —C(=O)—O-A, —C(=O)—N(A')A, C(A')(=N—OA), N(A')A, N(A')-C(=O)-A or S(=O)$_m$-A;

m is 0, 1 or 2;

A, A', A" independently of one another are hydrogen, $C_1$-$C_6$-alkyl, $C_2$-$C_6$-alkenyl, $C_2$-$C_6$-alkynyl, where the organic radicals may be partially or fully halogenated or may be substituted by cyano or $C_1$-$C_4$-alkoxy, or A and A' together with the atoms to which they are attached are a five- or six-membered saturated heterocycle which contains one to four heteroatoms from the group consisting of O, N and S.

Especially preferred are pyrimidines I where the substituents $L^1$ to $L^5$ are as defined below:

L is halogen, cyano, $C_1$-$C_8$-alkyl, $C_1$-$C_6$-alkoxy, —C(=O)—O-A, —C(=O)—N(A')A, A, A', A" independently of one another are hydrogen, $C_1$-$C_6$-alkyl, $C_2$-$C_6$-alkenyl, $C_2$-$C_6$-alkynyl.

Particular preference is given to compounds I in which $R''$ is halogen, cyano, $C_1$-$C_8$-alkyl, $C_2$-$C_{10}$-alkenyl, $C_2$-$C_{10}$-alkynyl, $C_1$-$C_6$-alkoxy, $C_2$-$C_{10}$-alkenyloxy, $C_2$-$C_{10}$-alkynyloxy, —C(=O)—O-A, —C(=O)—N(A')A, C(A')(=N—OA), where the aliphatic or alicyclic groups for their part may be partially or fully halogenated.

Especially preferred are compounds I in which $R''$ is halogen, cyano, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy.

Moreover, preference is given to pyrimidines I where the phenyl group substituted by $L_n$ is the group B

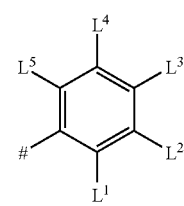

B where # is the point of attachment to the pyrimidine skeleton and $L^1$ is fluorine, chlorine, $CH_3$ or $CF_3$;

$L^2$, $L^4$ independently of one another are hydrogen, $CH_3$ or fluorine;

$L^3$ is hydrogen, fluorine, chlorine, bromine, cyano, $CH_3$, $SCH_3$, $OCH_3$, $SO_2CH_3$, $CO$—$NH_2$, $CO$—$NHCH_3$, CO—NHC$_2$H$_5$, CO—N(CH$_3$)$_2$, NH—C(=O)CH$_3$, N(CH$_3$)—C(=O)CH$_3$ or COOCH$_3$ and L$^5$ is hydrogen, fluorine, chlorine or CH$_3$.

Particular preference is also given to compounds I in which R$^3$ is C$_1$-C$_4$-alkyl which may be substituted by halogen.

Moreover, particular preference is given to compounds I in which R$^3$ is halogen, cyano, C$_1$-C$_4$-alkyl or C$_1$-C$_4$-alkoxy.

Especially preferred are compounds I in which R$^3$ is methyl, cyano, methoxy or in particular chlorine.

Suitable with a view to their fungicidal action are pyrimidines of the formula I in which R$^4$ is

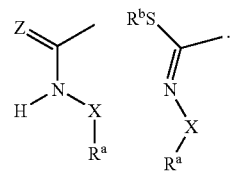

Preference is furthermore given to pyrimidines of the formula I in which R$^4$ is

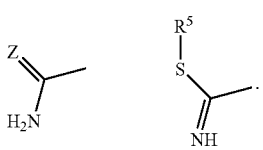

Especially preferred are pyrimidines of the formula I in which R$^4$ is

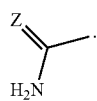

Finally, R$^4$ may preferably have the following meanings, which may also be understood as prodrug radical definitions (see Medicinal Research Reviews 2003, 23, 763-793, or J. of Pharmaceutical Sciences 1997, 86, 765-767):

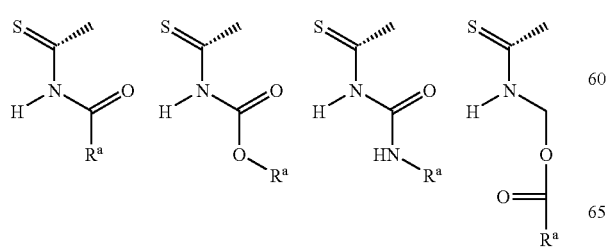

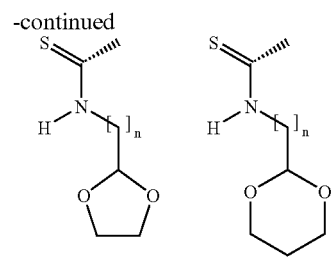

-continued

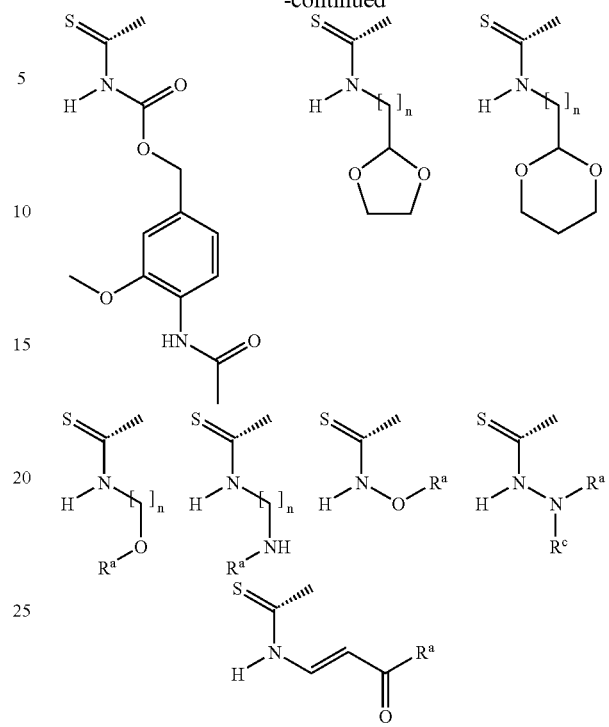

The index n in the alkenyl radicals of the above formulae is an integer from 1 to 3.

Particular preference is given to the radical definition R$^4$:

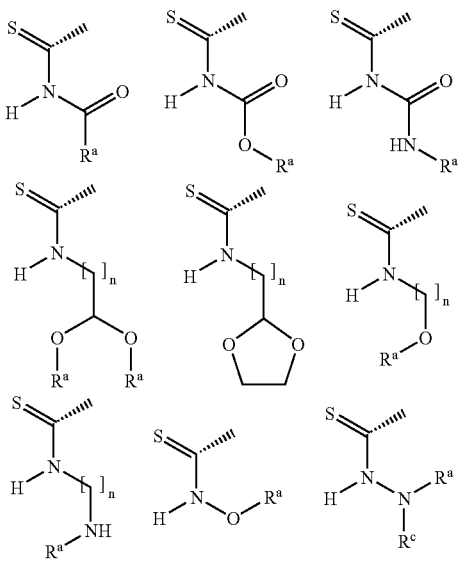

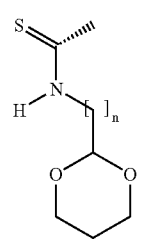

The bridge member X is preferably a direct bond and —(C=O)—.

The substituent $R^a$ is preferably hydrogen, methyl, allyl or propargyl and particularly preferably hydrogen.

The substituent $R^b$ is preferably hydrogen, $C_1$-$C_6$-alkyl or $C_2$-$C_6$-alkenyl and with particular preference methyl, allyl or propargyl.

The substituent $R^c$ is preferably hydrogen or methyl.

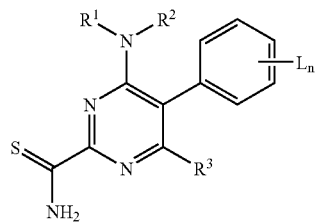
Ia

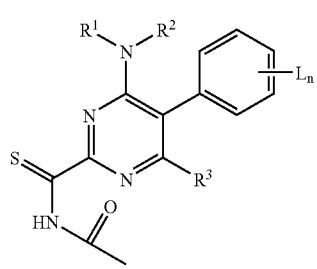
Ib

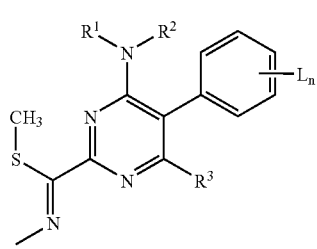
Ic

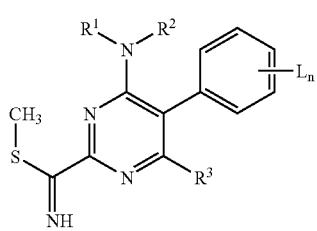
Id

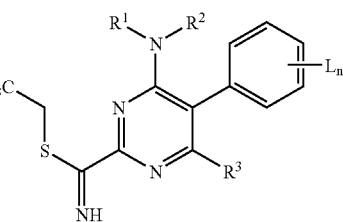
Ie

-continued

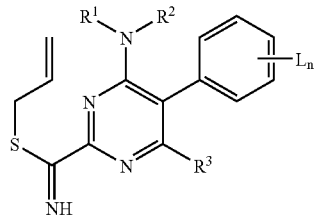
If

Table 1

Compounds of the formulae Ia, Ib, Ic, Id, Ie and If in which $L_n$ is 2-fluoro,6-chloro, $R^3$ is methyl and $R^1$, $R^2$ for each compound corresponds to one row of Table A Table 2

Compounds of the formulae Ia, Ib, Ic, Id, Ie and If in which $L_n$ is 2,6-difluoro, $R^3$ is methyl and $R^1$, $R^2$ for each compound corresponds to one row of Table A Table 3

Compounds of the formulae Ia, Ib, Ic, Id, Ie and If in which $L_n$ is 2,6-dichloro, $R^3$ is methyl and $R^1$, $R^2$ for each compound corresponds to one row of Table A Table 4

Compounds of the formulae Ia, Ib, Ic, Id, Ie and If in which $L_n$ is 2-fluoro,6-methyl, $R^3$ is methyl and $R^1$, $R^2$ for each compound corresponds to one row of Table A Table 5

Compounds of the formulae Ia, Ib, Ic, Id, Ie and If in which $L_n$ is 2,4,6-trifluoro, $R^3$ is methyl and $R^1$, $R^2$ for each compound corresponds to one row of Table A Table 6

Compounds of the formulae Ia, Ib, Ic, Id, Ie and If in which $L_n$ is 2-methyl,4-fluoro, $R^3$ is methyl and $R^1$, $R^2$ for each compound corresponds to one row of Table A Table 7

Compounds of the formulae Ia, Ib, Ic, Id, Ie and If in which $L_n$ is 2-fluoro,4-methoxycarbonyl, $R^3$ is methyl and $R^1$, $R^2$ for each compound corresponds to one row of Table A Table 8

Compounds of the formulae Ia, Ib, Ic, Id, Ie and If in which $L_n$ is 2-fluoro,4-CN, $R^3$ is methyl and $R^1$, $R^2$ for each compound corresponds to one row of Table A Table 9

Compounds of the formulae Ia, Ib, Ic, Id, Ie and If in which $L_n$ is 2,4,5-trifluoro, $R^3$ is methyl and $R^1$, $R^2$ for each compound corresponds to one row of Table A Table 10

Compounds of the formulae Ia, Ib, Ic, Id, Ie and If in which $L_n$ is 2,4-dichloro, $R^3$ is methyl and $R^1$, $R^2$ for each compound corresponds to one row of Table A Table 11
Compounds of the formulae Ia, Ib, Ic, Id, Ie and If in which $L_n$ is 2-chloro, $R^3$ is methyl and $R^1$, $R^2$ for each compound corresponds to one row of Table A Table 12
Compounds of the formulae Ia, Ib, Ic, Id, Ie and If in which $L_n$ is 2-fluoro, $R^3$ is methyl and $R^1$, $R^2$ for each compound corresponds to one row of Table A Table 13
Compounds of the formulae Ia, Ib, Ic, Id, Ie and If in which $L_n$ is 2,4-difluoro, $R^3$ is methyl and $R^1$, $R^2$ for each compound corresponds to one row of Table A Table 14
Compounds of the formulae Ia, Ib, Ic, Id, Ie and If in which $L_n$ is 2-fluoro, 4-chloro, $R^3$ is methyl and $R^1$, $R^2$ for each compound corresponds to one row of Table A Table 15
Compounds of the formulae Ia, Ib, Ic, Id, Ie and If in which $L_n$ is 2-chloro, 4-fluoro, $R^3$ is methyl and $R^1$, $R^2$ for each compound corresponds to one row of Table A Table 16
Compounds of the formulae Ia, Ib, Ic, Id, Ie and If in which $L_n$ is 2,3-difluoro, $R^3$ is methyl and $R^1$, $R^2$ for each compound corresponds to one row of Table A Table 17
Compounds of the formulae Ia, Ib, Ic, Id, Ie and If in which $L_n$ is 2,5-difluoro, $R^3$ is methyl and $R^1$, $R^2$ for each compound corresponds to one row of Table A Table 18
Compounds of the formulae Ia, Ib, Ic, Id, Ie and If in which $L_n$ is 2,3,4-trifluoro, $R^3$ is methyl and $R^1$, $R^2$ for each compound corresponds to one row of Table A Table 19
Compounds of the formulae Ia, Ib, Ic, Id, Ie and If in which $L_n$ is 2-methyl, $R^3$ is methyl and $R^1$, $R^2$ for each compound corresponds to one row of Table A Table 20
Compounds of the formulae Ia, Ib, Ic, Id, Ie and If in which $L_n$ is 2,4-dimethyl, $R^3$ is methyl and $R^1$, $R^2$ for each compound corresponds to one row of Table A Table 21
Compounds of the formulae Ia, Ib, Ic, Id, Ie and If in which $L_n$ is 2-methyl,4-chloro, $R^3$ is methyl and $R^1$, $R^2$ for each compound corresponds to one row of Table A Table 22
Compounds of the formulae Ia, Ib, Ic, Id, Ie and If in which $L_n$ is 2-fluoro,4-methyl, $R^3$ is methyl and $R^1$, $R^2$ for each compound corresponds to one row of Table A Table 23
Compounds of the formulae Ia, Ib, Ic, Id, Ie and If in which $L_n$ is 2,6-dimethyl, $R^3$ is methyl and $R^1$, $R^2$ for each compound corresponds to one row of Table A Table 24
Compounds of the formulae Ia, Ib, Ic, Id, Ie and If in which $L_n$ is 2,4,6-trimethyl, $R^3$ is methyl and $R^1$, $R^2$ for each compound corresponds to one row of Table A Table 25
Compounds of the formulae Ia, Ib, Ic, Id, Ie and If in which $L_n$ is 2,6-difluoro,4-cyano, $R^3$ is methyl and $R^1$, $R^2$ for each compound corresponds to one row of Table A Table 26
Compounds of the formulae Ia, Ib, Ic, Id, Ie and If in which $L_n$ is 2,6-difluoro,4-methyl, $R^3$ is methyl and $R^1$, $R^2$ for each compound corresponds to one row of Table A Table 27
Compounds of the formulae Ia, Ib, Ic, Id, Ie and If in which $L_n$ is 2,6-difluoro,4-methoxycarbonyl, $R^3$ is methyl and $R^1$, $R^2$ for each compound corresponds to one row of Table A Table 28
Compounds of the formulae Ia, Ib, Ic, Id, Ie and If in which $L_n$ is 2-chloro,4-methoxy, $R^3$ is methyl and $R^1$, $R^2$ for each compound corresponds to one row of Table A Table 29
Compounds of the formulae Ia, Ib, Ic, Id, Ie and If in which $L_n$ is 2-chloro,4-methyl, $R^3$ is methyl and $R^1$, $R^2$ for each compound corresponds to one row of Table A Table 30
Compounds of the formulae Ia, Ib, Ic, Id, Ie and If in which $L_n$ is 2-chloro,4-methoxycarbonyl, $R^3$ is methyl and $R^1$, $R^2$ for each compound corresponds to one row of Table A Table 31
Compounds of the formulae Ia, Ib, Ic, Id, Ie and If in which $L_n$ is 2-chloro,4-bromo, $R^3$ is methyl and $R^1$, $R^2$ for each compound corresponds to one row of Table A Table 32
Compounds of the formulae Ia, Ib, Ic, Id, Ie and If in which $L_n$ is 2-chloro,4-cyano, $R^3$ is methyl and $R^1$, $R^2$ for each compound corresponds to one row of Table A Table 33
Compounds of the formulae Ia, Ib, Ic, Id, Ie and If in which $L_n$ is 2,6-difluoro,4-methoxy, $R^3$ is methyl and $R^1$, $R^2$ for each compound corresponds to one row of Table A Table 34
Compounds of the formulae Ia, Ib, Ic, Id, Ie and If in which $L_n$ is 2-fluoro,3-methyl, $R^3$ is methyl and $R^1$, $R^2$ for each compound corresponds to one row of Table A Table 35
Compounds of the formulae Ia, Ib, Ic, Id, Ie and If in which $L_n$ is 2,5-dimethyl, $R^3$ is methyl and $R^1$, $R^2$ for each compound corresponds to one row of Table A Table 36
Compounds of the formulae Ia, Ib, Ic, Id, Ie and If in which $L_n$ is 2-methyl,4-cyano, $R^3$ is methyl and $R^1$, $R^2$ for each compound corresponds to one row of Table A Table 37
Compounds of the formulae Ia, Ib, Ic, Id, Ie and If in which $L_n$ is 2-methyl,4-bromo, $R^3$ is methyl and $R^1$, $R^2$ for each compound corresponds to one row of Table A Table 38
Compounds of the formulae Ia, Ib, Ic, Id, Ie and If in which $L_n$ is 2-methyl,5-fluoro, $R^3$ is methyl and $R^1$, $R^2$ for each compound corresponds to one row of Table A Table 39
Compounds of the formulae Ia, Ib, Ic, Id, Ie and If in which $L_n$ is 2-methyl,4-methoxy, $R^3$ is methyl and $R^1$, $R^2$ for each compound corresponds to one row of Table A Table 40
Compounds of the formulae Ia, Ib, Ic, Id, Ie and If in which $L_n$ is 2-methyl, 4-methoxycarbonyl, $R^3$ is methyl and $R^1$, $R^2$ for each compound corresponds to one row of Table A Table 41
Compounds of the formulae Ia, Ib, Ic, Id, Ie and If in which $L_n$ is 2,5-dimethyl,4-bromo, $R^3$ is methyl and $R^1$, $R^2$ for each compound corresponds to one row of Table A Table 42
Compounds of the formulae Ia, Ib, Ic, Id, Ie and If in which $L_n$ is 2-fluoro,4-bromo, $R^3$ is methyl and $R^1$, $R^2$ for each compound corresponds to one row of Table A Table 43
Compounds of the formulae Ia, Ib, Ic, Id, Ie and If in which $L_n$ is 2-fluoro,4-methoxy, $R^3$ is methyl and $R^1$, $R^2$ for each compound corresponds to one row of Table A Table 44
Compounds of the formulae Ia, Ib, Ic, Id, Ie and If in which $L_n$ is 2-fluoro,5-methyl, $R^3$ is methyl and $R^1$, $R^2$ for each compound corresponds to one row of Table A Table 45
Compounds of the formulae Ia, Ib, Ic, Id, Ie and If in which $L_n$ is pentafluoro, $R^3$ is methyl and $R^1$, $R^2$ for each compound corresponds to one row of Table A Table 46
Compounds of the formulae Ia, Ib, Ic, Id, Ie and If in which $L_n$ is 2-fluor,6-chloro, $R^3$ is chloro and $R^1$, $R^2$ for each compound corresponds to one row of Table A Table 47
Compounds of the formulae Ia, Ib, Ic, Id, Ie and If in which $L_n$ is 2,6-difluoro, $R^3$ is chloro and $R^1$, $R^2$ for each compound corresponds to one row of Table A Table 48
Compounds of the formulae Ia, Ib, Ic, Id, Ie and If in which $L_n$ is 2,6-dichloro, $R^3$ is chloro and $R^1$, $R^2$ for each compound corresponds to one row of Table A Table 49
Compounds of the formulae Ia, Ib, Ic, Id, Ie and If in which $L_n$ is 2-fluoro,6-methyl, $R^3$ is chloro and $R^1$, $R^2$ for each compound corresponds to one row of Table A Table 50
Compounds of the formulae Ia, Ib, Ic, Id, Ie and If in which $L_n$ is 2,4,6-trifluoro, $R^3$ is chloro and $R^1$, $R^2$ for each compound corresponds to one row of Table A Table 51
Compounds of the formulae Ia, Ib, Ic, Id, Ie and If in which $L_n$ is 2-methyl,4-fluoro, $R^3$ is chloro and $R^1$, $R^2$ for each compound corresponds to one row of Table A Table 52
Compounds of the formulae Ia, Ib, Ic, Id, Ie and If in which $L_n$ is 2-fluoro,4-methoxycarbonyl, $R^3$ is chloro and $R^1$, $R^2$ for each compound corresponds to one row of Table A Table 53
Compounds of the formulae Ia, Ib, Ic, Id, Ie and If in which $L_n$ is 2-fluoro,4-CN, $R^3$ is chloro and $R^1$, $R^2$ for each compound corresponds to one row of Table A Table 54
Compounds of the formulae Ia, Ib, Ic, Id, Ie and If in which $L_n$ is 2,4,5-trifluoro, $R^3$ is chloro and $R^1$, $R^2$ for each compound corresponds to one row of Table A Table 55
Compounds of the formulae Ia, Ib, Ic, Id, Ie and If in which $L_n$ is 2,4-dichloro, $R^3$ is chloro and $R^1$, $R^2$ for each compound corresponds to one row of Table A Table 56
Compounds of the formulae Ia, Ib, Ic, Id, Ie and If in which $L_n$ is 2-chloro, $R^3$ is chloro and $R^1$, $R^2$ for each compound corresponds to one row of Table A Table 57
Compounds of the formulae Ia, Ib, Ic, Id, Ie and If in which $L_n$ is 2-fluoro, $R^3$ is chloro and $R^1$, $R^2$ for each compound corresponds to one row of Table A Table 58
Compounds of the formulae Ia, Ib, Ic, Id, Ie and If in which $L_n$ is 2,4-difluoro, $R^3$ is chloro and $R^1$, $R^2$ for each compound corresponds to one row of Table A Table 59
Compounds of the formulae Ia, Ib, Ic, Id, Ie and If in which $L_n$ is 2-fluoro,4-chloro, $R^3$ is chloro and $R^1$, $R^2$ for each compound corresponds to one row of Table A Table 60
Compounds of the formulae Ia, Ib, Ic, Id, Ie and If in which $L_n$ is 2-chloro,4-fluoro, $R^3$ is chloro and $R^1$, $R^2$ for each compound corresponds to one row of Table A Table 61
Compounds of the formulae Ia, Ib, Ic, Id, Ie and If in which $L_n$ is 2,3-difluoro, $R^3$ is chloro and $R^1$, $R^2$ for each compound corresponds to one row of Table A Table 62
Compounds of the formulae Ia, Ib, Ic, Id, Ie and If in which $L_n$ is 2,5-difluoro, $R^3$ is chloro and $R^1$, $R^2$ for each compound corresponds to one row of Table A Table 63
Compounds of the formulae Ia, Ib, Ic, Id, Ie and If in which $L_n$ is 2,3,4-trifluoro, $R^3$ is chloro and $R^1$, $R^2$ for each compound corresponds to one row of Table A Table 64
Compounds of the formulae Ia, Ib, Ic, Id, Ie and If in which $L_n$ is 2-methyl, $R^3$ is chloro and $R^1$, $R^2$ for each compound corresponds to one row of Table A Table 65
Compounds of the formulae Ia, Ib, Ic, Id, Ie and If in which $L_n$ is 2,4-dimethyl, $R^3$ is chloro and $R^1$, $R^2$ for each compound corresponds to one row of Table A Table 66
Compounds of the formulae Ia, Ib, Ic, Id, Ie and If in which $L_n$ is 2-methyl,4-chloro, $R^3$ is chloro and $R^1$, $R^2$ for each compound corresponds to one row of Table A Table 67
Compounds of the formulae Ia, Ib, Ic, Id, Ie and If in which $L_n$ is 2-fluoro,4-methyl, $R^3$ is chloro and $R^1$, $R^2$ for each compound corresponds to one row of Table A Table 68
Compounds of the formulae Ia, Ib, Ic, Id, Ie and If in which $L_n$ is 2,6-dimethyl, $R^3$ is chloro and $R^1$, $R^2$ for each compound corresponds to one row of Table A Table 69
Compounds of the formulae Ia, Ib, Ic, Id, Ie and If in which $L_n$ is 2,4,6-trimethyl, $R^3$ is chloro and $R^1$, $R^2$ for each compound corresponds to one row of Table A Table 70
Compounds of the formulae Ia, Ib, Ic, Id, Ie and If in which $L_n$ is 2,6-difluoro,4-cyano, $R^3$ is chloro and $R^1$, $R^2$ for each compound corresponds to one row of Table A Table 71
Compounds of the formulae Ia, Ib, Ic, Id, Ie and If in which $L_n$ is 2,6-difluoro,4-methyl, $R^3$ is chloro and $R^1$, $R^2$ for each compound corresponds to one row of Table A Table 72
Compounds of the formulae Ia, Ib, Ic, Id, Ie and If in which $L_n$ is 2,6-difluoro,4-methoxycarbonyl, $R^3$ is chloro and $R^1$, $R^2$ for each compound corresponds to one row of Table A Table 73
Compounds of the formulae Ia, Ib, Ic, Id, Ie and If in which $L_n$ is 2-chloro,4-methoxy, $R^3$ is chloro and $R^1$, $R^2$ for each compound corresponds to one row of Table A Table 74
Compounds of the formulae Ia, Ib, Ic, Id, Ie and If in which $L_n$ is 2-chloro,4-methyl, $R^3$ is chloro and $R^1$, $R^2$ for each compound corresponds to one row of Table A Table 75
Compounds of the formulae Ia, Ib, Ic, Id, Ie and If in which $L_n$ is 2-chloro,4-methoxycarbonyl, $R^3$ is chloro and $R^1$, $R^2$ for each compound corresponds to one row of Table A Table 76
Compounds of the formulae Ia, Ib, Ic, Id, Ie and If in which $L_n$ is 2-chloro,4-bromo, $R^3$ is chloro and $R^1$, $R^2$ for each compound corresponds to one row of Table A Table 77
Compounds of the formulae Ia, Ib, Ic, Id, Ie and If in which $L_n$ is 2-chloro,4-cyano, $R^3$ is chloro and $R^1$, $R^2$ for each compound corresponds to one row of Table A Table 78
Compounds of the formulae Ia, Ib, Ic, Id, Ie and If in which $L_n$ is 2,6-difluoro,4-methoxy, $R^3$ is chloro and $R^1$, $R^2$ for each compound corresponds to one row of Table A Table 79
Compounds of the formulae Ia, Ib, Ic, Id, Ie and If in which $L_n$ is 2-fluoro,3-methyl, $R^3$ is chloro and $R^1$, $R^2$ for each compound corresponds to one row of Table A Table 80
Compounds of the formulae Ia, Ib, Ic, Id, Ie and If in which $L_n$ is 2,5-dimethyl, $R^3$ is chloro and $R^1$, $R^2$ for each compound corresponds to one row of Table A Table 81
Compounds of the formulae Ia, Ib, Ic, Id, Ie and If in which $L_n$ is 2-methyl,4-cyano, $R^3$ is chloro and $R^1$, $R^2$ for each compound corresponds to one row of Table A Table 82
Compounds of the formulae Ia, Ib, Ic, Id, Ie and If in which $L_n$ is 2-methyl,4-bromo, $R^3$ is chloro and $R^1$, $R^2$ for each compound corresponds to one row of Table A Table 83
Compounds of the formulae Ia, Ib, Ic, Id, Ie and If in which $L_n$ is 2-methyl,5-fluoro, $R^3$ is chloro and $R^1$, $R^2$ for each compound corresponds to one row of Table A Table 84
Compounds of the formulae Ia, Ib, Ic, Id, Ie and If in which $L_n$ is 2-methyl,4-methoxy, $R^3$ is chloro and $R^1$, $R^2$ for each compound corresponds to one row of Table A Table 85
Compounds of the formulae Ia, Ib, Ic, Id, Ie and If in which $L_n$ is 2-methyl,4-methoxycarbonyl, $R^3$ is chloro and $R^1$, $R^2$ for each compound corresponds to one row of Table A Table 86
Compounds of the formulae Ia, Ib, Ic, Id, Ie and If in which $L_n$ is 2,5-dimethyl,4-bromo, $R^3$ is chloro and $R^1$, $R^2$ for each compound corresponds to one row of Table A Table 87
Compounds of the formulae Ia, Ib, Ic, Id, Ie and If in which $L_n$ is 2-fluoro,4-bromo, $R^3$ is chloro and $R^1$, $R^2$ for each compound corresponds to one row of Table A Table 88
Compounds of the formulae Ia, Ib, Ic, Id, Ie and If in which $L_n$ is 2-fluoro,4-methoxy, $R^3$ is chloro and $R^1$, $R^2$ for each compound corresponds to one row of Table A Table 89
Compounds of the formulae Ia, Ib, Ic, Id, Ie and If in which $L_n$ is 2-fluoro,5-methyl, $R^3$ is chloro and $R^1$, $R^2$ for each compound corresponds to one row of Table A Table 90
Compounds of the formulae Ia, Ib, Ic, Id, Ie and If in which $L_n$ is pentafluoro, $R^3$ is chloro and $R^1$, $R^2$ for each compound corresponds to one row of Table A Table 91
Compounds of the formulae Ia, Ib, Ic, Id, Ie and If in which $L_n$ is 2-fluoro,6-chloro, $R^3$ is methoxy and $R^1$, $R^2$ for each compound corresponds to one row of Table A Table 92
Compounds of the formulae Ia, Ib, Ic, Id, Ie and If in which $L_n$ is 2,6-difluoro, $R^3$ is methoxy and $R^1$, $R^2$ for each compound corresponds to one row of Table A Table 93
Compounds of the formulae Ia, Ib, Ic, Id, Ie and If in which $L_n$ is 2,6-dichloro, $R^3$ is methoxy and $R^1$, $R^2$ for each compound corresponds to one row of Table A Table 94
Compounds of the formulae Ia, Ib, Ic, Id, Ie and If in which $L_n$ is 2-fluoro,6-methyl, $R^3$ is methoxy and $R^1$, $R^2$ for each compound corresponds to one row of Table A Table 95
Compounds of the formulae Ia, Ib, Ic, Id, Ie and If in which $L_n$ is 2,4,6-trifluoro, $R^3$ is methoxy and $R^1$, $R^2$ for each compound corresponds to one row of Table A Table 96
Compounds of the formulae Ia, Ib, Ic, Id, Ie and If in which $L_n$ is 2-methyl,4-fluoro, $R^3$ is methoxy and $R^1$, $R^2$ for each compound corresponds to one row of Table A Table 97
Compounds of the formulae Ia, Ib, Ic, Id, Ie and If in which $L_n$ is 2-fluoro,4-methoxycarbonyl, $R^3$ is methoxy and $R^1$, $R^2$ for each compound corresponds to one row of Table A Table 98
Compounds of the formulae Ia, Ib, Ic, Id, Ie and If in which $L_n$ is 2-fluoro,4-CN, $R^3$ is methoxy and $R^1$, $R^2$ for each compound corresponds to one row of Table A Table 99
Compounds of the formulae Ia, Ib, Ic, Id, Ie and If in which $L_n$ is 2,4,5-trifluoro, $R^3$ is methoxy and $R^1$, $R^2$ for each compound corresponds to one row of Table A Table 100
Compounds of the formulae Ia, Ib, Ic, Id, Ie and If in which $L_n$ is 2,4-dichloro, $R^3$ is methoxy and $R^1$, $R^2$ for each compound corresponds to one row of Table A Table 101
Compounds of the formulae Ia, Ib, Ic, Id, Ie and If in which $L_n$ is 2-chloro, $R^3$ is methoxy and $R^1$, $R^2$ for each compound corresponds to one row of Table A Table 102
Compounds of the formulae Ia, Ib, Ic, Id, Ie and If in which $L_n$ is 2-fluoro, $R^3$ is methoxy and $R^1$, $R^2$ for each compound corresponds to one row of Table A Table 103
Compounds of the formulae Ia, Ib, Ic, Id, Ie and If in which $L_n$ is 2,4-difluoro, $R^3$ is methoxy and $R^1$, $R^2$ for each compound corresponds to one row of Table A Table 104
Compounds of the formulae Ia, Ib, Ic, Id, Ie and If in which $L_n$ is 2-fluoro,4-chloro, $R^3$ is methoxy and $R^1$, $R^2$ for each compound corresponds to one row of Table A Table 105
Compounds of the formulae Ia, Ib, Ic, Id, Ie and If in which $L_n$ is 2-chloro,4-fluoro, $R^3$ is methoxy and $R^1$, $R^2$ for each compound corresponds to one row of Table A Table 106
Compounds of the formulae Ia, Ib, Ic, Id, Ie and If in which $L_n$ is 2,3-difluoro, $R^3$ is methoxy and $R^1$, $R^2$ for each compound corresponds to one row of Table A Table 107
Compounds of the formulae Ia, Ib, Ic, Id, Ie and If in which $L_n$ is 2,5-difluoro, $R^3$ is methoxy and $R^1$, $R^2$ for each compound corresponds to one row of Table A Table 108
Compounds of the formulae Ia, Ib, Ic, Id, Ie and If in which $L_n$ is 2,3,4-trifluoro, $R^3$ is methoxy and $R^1$, $R^2$ for each compound corresponds to one row of Table A Table 109
Compounds of the formulae Ia, Ib, Ic, Id, Ie and If in which $L_n$ is 2-methyl, $R^3$ is methoxy and $R^1$, $R^2$ for each compound corresponds to one row of Table A Table 110
Compounds of the formulae Ia, Ib, Ic, Id, Ie and If in which $L_n$ is 2,4-dimethyl, $R^3$ is methoxy and $R^1$, $R^2$ for each compound corresponds to one row of Table A Table 111
Compounds of the formulae Ia, Ib, Ic, Id, Ie and If in which $L_n$ is 2-methyl,4-chloro, $R^3$ is methoxy and $R^1$, $R^2$ for each compound corresponds to one row of Table A Table 112
Compounds of the formulae Ia, Ib, Ic, Id, Ie and If in which $L_n$ is 2-fluoro,4-methyl, $R^3$ is methoxy and $R^1$, $R^2$ for each compound corresponds to one row of Table A Table 113
Compounds of the formulae Ia, Ib, Ic, Id, Ie and If in which $L_n$ is 2,6-dimethyl, $R^3$ is methoxy and $R^1$, $R^2$ for each compound corresponds to one row of Table A Table 114
Compounds of the formulae Ia, Ib, Ic, Id, Ie and If, in which $L_n$ is 2,4,6-trimethyl, $R^3$ is methoxy and $R^1$, $R^2$ for each compound corresponds to one row of Table A Table 115
Compounds of the formulae Ia, Ib, Ic, Id, Ie and If in which $L_n$ is 2,6-difluoro,4-cyano, $R^3$ is methoxy and $R^1$, $R^2$ for each compound corresponds to one row of Table A Table 116
Compounds of the formulae Ia, Ib, Ic, Id, Ie and If in which $L_n$ is 2,6-difluoro,4-methyl, $R^3$ is methoxy and $R^1$, $R^2$ for each compound corresponds to one row of Table A Table 117
Compounds of the formulae Ia, Ib, Ic, Id, Ie and If in which $L_n$ is 2,6-difluoro,4-methoxycarbonyl, $R^3$ is methoxy and $R^1$, $R^2$ for each compound corresponds to one row of Table A Table 118
Compounds of the formulae Ia, Ib, Ic, Id, Ie and If in which $L_n$ is 2-chloro,4-methoxy, $R^3$ is methoxy and $R^1$, $R^2$ for each compound corresponds to one row of Table A Table 119
Compounds of the formulae Ia, Ib, Ic, Id, Ie and If in which $L_n$ is 2-chloro,4-methyl, $R^3$ is methoxy and $R^1$, $R^2$ for each compound corresponds to one row of Table A Table 120
Compounds of the formulae Ia, Ib, Ic, Id, Ie and If in which $L_n$ is 2-chloro,4-methoxycarbonyl, $R^3$ is methoxy and $R^1$, $R^2$ for each compound corresponds to one row of Table A Table 121
Compounds of the formulae Ia, Ib, Ic, Id, Ie and If in which $L_n$ is 2-chloro,4-methoxy, $R^3$ is methoxy and $R^1$, $R^2$ for each compound corresponds to one row of Table A Table 122
Compounds of the formulae Ia, Ib, Ic, Id, Ie and If in which $L_n$ is 2-chloro,4-cyano, $R^3$ is methoxy and $R^1$, $R^2$ for each compound corresponds to one row of Table A Table 123
Compounds of the formulae Ia, Ib, Ic, Id, Ie and If in which $L_n$ is 2,6-difluoro,4-methoxy, $R^3$ is methoxy and $R^1$, $R^2$ for each compound corresponds to one row of Table A Table 124
Compounds of the formulae Ia, Ib, Ic, Id, Ie and If in which $L_n$ is 2-fluoro,3-methyl, $R^3$ is methoxy and $R^1$, $R^2$ for each compound corresponds to one row of Table A Table 125
Compounds of the formulae Ia, Ib, Ic, Id, Ie and If in which $L_n$ is 2,5-dimethyl, $R^3$ is methoxy and $R^1$, $R^2$ for each compound corresponds to one row of Table A Table 126
Compounds of the formulae Ia, Ib, Ic, Id, Ie and If in which $L_n$ is 2-methyl,4-cyano, $R^3$ is methoxy and $R^1$, $R^2$ for each compound corresponds to one row of Table A Table 127
Compounds of the formulae Ia, Ib, Ic, Id, Ie and If in which $L_n$ is 2-methyl,4-bromo, $R^3$ is methoxy and $R^1$, $R^2$ for each compound corresponds to one row of Table A Table 128
Compounds of the formulae Ia, Ib, Ic, Id, Ie and If in which $L_n$ is 2-methyl,5-fluoro, $R^3$ is methoxy and $R^1$, $R^2$ for each compound corresponds to one row of Table A Table 129
Compounds of the formulae Ia, Ib, Ic, Id, Ie and If in which $L_n$ is 2-methyl,4-methoxy, $R^3$ is methoxy and $R^1$, $R^2$ for each compound corresponds to one row of Table A Table 130
Compounds of the formulae Ia, Ib, Ic, Id, Ie and If, in which $L_n$ is 2-methyl,4-methoxycarbonyl, $R^3$ is methoxy and $R^1$, $R^2$ for each compound corresponds to one row of Table A Table 131
Compounds of the formulae Ia, Ib, Ic, Id, Ie and If in which $L_n$ is 2,5-dimethyl,4-bromo, $R^3$ is methoxy and $R^1$, $R^2$ for each compound corresponds to one row of Table A Table 132
Compounds of the formulae Ia, Ib, Ic, Id, Ie and If in which $L_n$ is 2-fluoro,4-bromo, $R^3$ is methoxy and $R^1$, $R^2$ for each compound corresponds to one row of Table A Table 133
Compounds of the formulae Ia, Ib, Ic, Id, Ie and If in which $L_n$ is 2-fluoro,4-methoxy, $R^3$ is methoxy and $R^1$, $R^2$ for each compound corresponds to one row of Table A Table 134
Compounds of the formulae Ia, Ib, Ic, Id, Ie and If in which $L_n$ is 2-fluoro,5-methyl, $R^3$ is methoxy and $R^1$, $R^2$ for each compound corresponds to one row of Table A Table 135
Compounds of the formulae Ia, Ib, Ic, Id, Ie and If in which $L_n$ is pentafluoro, $R^3$ is methoxy and $R^1$, $R^2$ for each compound corresponds to one row of Table A Table 136
Compounds of the formulae Ia, Ib, Ic, Id, Ie and If in which $L_n$ is 2-fluoro,6-chloro, $R^3$ is cyano and $R^1$, $R^2$ for each compound corresponds to one row of Table A Table 137
Compounds of the formulae Ia, Ib, Ic, Id, Ie and If in which $L_n$ is 2,6-difluoro, $R^3$ is cyano and $R^1$, $R^2$ for each compound corresponds to one row of Table A Table 138
Compounds of the formulae Ia, Ib, Ic, Id, Ie and If in which $L_n$ is 2,6-difluoro, $R^3$ is cyano and $R^1$, $R^2$ for each compound corresponds to one row of Table A Table 139
Compounds of the formulae Ia, Ib, Ic, Id, Ie and If in which $L_n$ is 2-fluoro,6-methyl, $R^3$ is cyano and $R^1$, $R^2$ for each compound corresponds to one row of Table A Table 140
Compounds of the formulae Ia, Ib, Ic, Id, Ie and If in which $L_n$ is 2,4,6-trifluoro, $R^3$ is cyano and $R^1$, $R^2$ for each compound corresponds to one row of Table A Table 141
Compounds of the formulae Ia, Ib, Ic, Id, Ie and If in which $L_n$ is 2-methyl,4-fluoro, $R^3$ is cyano and $R^1$, $R^2$ for each compound corresponds to one row of Table A Table 142
Compounds of the formulae Ia, Ib, Ic, Id, Ie and If in which $L_n$ is 2-fluoro,4-methoxycarbonyl, $R^3$ is cyano and $R^1$, $R^2$ for each compound corresponds to one row of Table A Table 143
Compounds of the formulae Ia, Ib, Ic, Id, Ie and If in which $L_n$ is 2-fluoro,4-CN, $R^3$ is cyano and $R^1$, $R^2$ for each compound corresponds to one row of Table A Table 144
Compounds of the formulae Ia, Ib, Ic, Id, Ie and If in which $L_n$ is 2,4,5-trifluoro, $R^3$ is cyano and $R^1$, $R^2$ for each compound corresponds to one row of Table A Table 145
Compounds of the formulae Ia, Ib, Ic, Id, Ie and If in which $L_n$ is 2,4-dichloro, $R^3$ is cyano and $R^1$, $R^2$ for each compound corresponds to one row of Table A Table 146
Compounds of the formulae Ia, Ib, Ic, Id, Ie and If, in which $L_n$ is 2-chloro, $R^3$ is cyano and $R^1$, $R^2$ for each compound corresponds to one row of Table A Table 147
Compounds of the formulae Ia, Ib, Ic, Id, Ie and If in which $L_n$ is 2-fluoro, $R^3$ is cyano and $R^1$, $R^2$ for each compound corresponds to one row of Table A Table 148
Compounds of the formulae Ia, Ib, Ic, Id, Ie and If in which $L_n$ is 2,4-difluoro, $R^3$ is cyano and $R^1$, $R^2$ for each compound corresponds to one row of Table A Table 149
Compounds of the formulae Ia, Ib, Ic, Id, Ie and If in which $L_n$ is 2-fluoro,4-chloro, $R^3$ is cyano and $R^1$, $R^2$ for each compound corresponds to one row of Table A Table 150
Compounds of the formulae Ia, Ib, Ic, Id, Ie and If in which $L_n$ is 2-chloro,4-fluoro, $R^3$ is cyano and $R^1$, $R^2$ for each compound corresponds to one row of Table A Table 151
Compounds of the formulae Ia, Ib, Ic, Id, Ie and If in which $L_n$ is 2,3-difluoro, $R^3$ is cyano and $R^1$, $R^2$ for each compound corresponds to one row of Table A Table 152
Compounds of the formulae Ia, Ib, Ic, Id, Ie and If in which $L_n$ is 2,5-difluoro, $R^3$ is cyano and $R^1$, $R^2$ for each compound corresponds to one row of Table A Table 153
Compounds of the formulae Ia, Ib, Ic, Id, Ie and If in which $L_n$ is 2,3,4-trifluoro, $R^3$ is cyano and $R^1$, $R^2$ for each compound corresponds to one row of Table A Table 154
Compounds of the formulae Ia, Ib, Ic, Id, Ie and If in which $L_n$ is 2-methyl, $R^3$ is cyano and $R^1$, $R^2$ for each compound corresponds to one row of Table A Table 155
Compounds of the formulae Ia, Ib, Ic, Id, Ie and If in which $L_n$ is 2,4-dimethyl, $R^3$ is cyano and $R^1$, $R^2$ for each compound corresponds to one row of Table A Table 156
Compounds of the formulae Ia, Ib, Ic, Id, Ie and If in which $L_n$ is 2-methyl,4-chloro, $R^3$ is cyano and $R^1$, $R^2$ for each compound corresponds to one row of Table A Table 157
Compounds of the formulae Ia, Ib, Ic, Id, Ie and If in which $L_n$ is 2-fluoro,4-methyl, $R^3$ is cyano and $R^1$, $R^2$ for each compound corresponds to one row of Table A Table 158
Compounds of the formulae Ia, Ib, Ic, Id, Ie and If in which $L_n$ is 2,6-dimethyl, $R^3$ is cyano and $R^1$, $R^2$ for each compound corresponds to one row of Table A Table 159
Compounds of the formulae Ia, Ib, Ic, Id, Ie and If in which $L_n$ is 2,4,6-trimethyl, $R^3$ is cyano and $R^1$, $R^2$ for each compound corresponds to one row of Table A Table 160
Compounds of the formulae Ia, Ib, Ic, Id, Ie and If in which $L_n$ is 2,6-difluoro,4-cyano, $R^3$ is cyano and $R^1$, $R^2$ for each compound corresponds to one row of Table A Table 161
Compounds of the formulae Ia, Ib, Ic, Id, Ie and If in which $L_n$ is 2,6-difluoro,4-methyl, $R^3$ is cyano and $R^1$, $R^2$ for each compound corresponds to one row of Table A Table 162
Compounds of the formulae Ia, Ib, Ic, Id, Ie and If in which $L_n$ is 2,6-difluoro,4-methoxycarbonyl, $R^3$ is cyano and $R^1$, $R^2$ for each compound corresponds to one row of Table A Table 163
Compounds of the formulae Ia, Ib, Ic, Id, Ie and If in which $L_n$ is 2-chloro,4-methoxy, $R^3$ is cyano and $R^1$, $R^2$ for each compound corresponds to one row of Table A Table 164
Compounds of the formulae Ia, Ib, Ic, Id, Ie and If in which $L_n$ is 2-chloro,4-methyl, $R^3$ is cyano and $R^1$, $R^2$ for each compound corresponds to one row of Table A Table 165
Compounds of the formulae Ia, Ib, Ic, Id, Ie and If in which $L_n$ is 2-chloro,4-methoxycarbonyl, $R^3$ is cyano and $R^1$, $R^2$ for each compound corresponds to one row of Table A Table 166
Compounds of the formulae Ia, Ib, Ic, Id, Ie and If in which $L_n$ is 2-chloro,4-bromo, $R^3$ is cyano and $R^1$, $R^2$ for each compound corresponds to one row of Table A Table 167
Compounds of the formulae Ia, Ib, Ic, Id, Ie and If in which $L_n$ is 2-chloro,4-cyano, $R^3$ is cyano and $R^1$, $R^2$ for each compound corresponds to one row of Table A Table 168
Compounds of the formulae Ia, Ib, Ic, Id, Ie and If in which $L_n$ is 2,6-difluoro,4-methoxy, $R^3$ is cyano and $R^1$, $R^2$ for each compound corresponds to one row of Table A Table 169
Compounds of the formulae Ia, Ib, Ic, Id, Ie and If in which $L_n$ is 2-fluoro,3-methyl, $R^3$ is cyano and $R^1$, $R^2$ for each compound corresponds to one row of Table A Table 170
Compounds of the formulae Ia, Ib, Ic, Id, Ie and If in which $L_n$ is 2,5-dimethyl, $R^3$ is cyano and $R^1$, $R^2$ for each compound corresponds to one row of Table A Table 171
Compounds of the formulae Ia, Ib, Ic, Id, Ie and If in which $L_n$ is 2-methyl,4-cyano, $R^3$ is cyano and $R^1$, $R^2$ for each compound corresponds to one row of Table A Table 172
Compounds of the formulae Ia, Ib, Ic, Id, Ie and If in which $L_n$ is 2-methyl,4-bromo, $R^3$ is cyano and $R^1$, $R^2$ for each compound corresponds to one row of Table A Table 173
Compounds of the formulae Ia, Ib, Ic, Id, Ie and If in which $L_n$ is 2-methyl,5-fluoro, $R^3$ is cyano and $R^1$, $R^2$ for each compound corresponds to one row of Table A Table 174
Compounds of the formulae Ia, Ib, Ic, Id, Ie and If in which $L_n$ is 2-methyl,4-methoxy, $R^3$ is cyano and $R^1$, $R^2$ for each compound corresponds to one row of Table A Table 175
Compounds of the formulae Ia, Ib, Ic, Id, Ie and If in which $L_n$ is 2-methyl,4-methoxycarbonyl, $R^3$ is cyano and $R^1$, $R^2$ for each compound corresponds to one row of Table A Table 176
Compounds of the formulae Ia, Ib, Ic, Id, Ie and If in which $L_n$ is 2,5-dimethyl,4-bromo, $R^3$ is cyano and $R^1$, $R^2$ for each compound corresponds to one row of Table A Table 177
Compounds of the formulae Ia, Ib, Ic, Id, Ie and If in which $L_n$ is 2-fluoro,4-bromo, $R^3$ is cyano and $R^1$, $R^2$ for each compound corresponds to one row of Table A Table 178
Compounds of the formulae Ia, Ib, Ic, Id, Ie and If in which $L_n$ is 2-fluoro,4-methoxy, $R^3$ is cyano and $R^1$, $R^2$ for each compound corresponds to one row of Table A Table 179
Compounds of the formulae Ia, Ib, Ic, Id, Ie and If in which $L_n$ is 2-fluoro,5-methyl, $R^3$ is cyano and $R^1$, $R^2$ for each compound corresponds to one row of Table A Table 180
Compounds of the formulae Ia, Ib, Ic, Id, Ie and If in which $L_n$ is pentafluoro, $R^3$ is cyano and $R^1$, $R^2$ for each compound corresponds to one row of Table A

TABLE A

| No. | R¹ | R² |
|---|---|---|
| A-1. | CH$_2$CH$_3$ | H |
| A-2. | CH$_2$CH$_3$ | CH$_3$ |
| A-3. | CH$_2$CH$_3$ | CH$_2$CH$_3$ |
| A-4. | CH$_2$CH$_2$CH$_3$ | H |
| A-5. | CH$_2$CH$_2$CH$_3$ | CH$_3$ |
| A-6. | CH$_2$CH$_2$CH$_3$ | CH$_2$CH$_3$ |
| A-7. | CH$_2$CH$_2$CH$_3$ | CH$_2$CH$_2$CH$_3$ |
| A-8. | CH$_2$CH$_2$F | H |
| A-9. | CH$_2$CH$_2$F | CH$_3$ |
| A-10. | CH$_2$CH$_2$F | CH$_2$CH$_3$ |
| A-11. | CH$_2$CF$_3$ | H |
| A-12. | CH$_2$CF$_3$ | CH$_3$ |
| A-13. | CH$_2$CF$_3$ | CH$_2$CH$_3$ |
| A-14. | CH$_2$CF$_3$ | CH$_2$CH$_2$CH$_3$ |
| A-15. | CH$_2$CCl$_3$ | H |
| A-16. | CH$_2$CCl$_3$ | CH$_3$ |
| A-17. | CH$_2$CCl$_3$ | CH$_2$CH$_3$ |
| A-18. | CH$_2$CCl$_3$ | CH$_2$CH$_2$CH$_3$ |
| A-19. | CH(CH$_3$)$_2$ | H |
| A-20. | CH(CH$_3$)$_2$ | CH$_3$ |
| A-21. | CH(CH$_3$)$_2$ | CH$_2$CH$_3$ |
| A-22. | CH(CH$_3$)$_2$ | CH$_2$CH$_2$CH$_3$ |
| A-23. | CH$_2$C(CH$_3$)$_3$ | H |
| A-24. | CH$_2$C(CH$_3$)$_3$ | CH$_3$ |
| A-25. | CH$_2$C(CH$_3$)$_3$ | CH$_2$CH$_3$ |
| A-26. | CH$_2$CH(CH$_3$)$_2$ | H |
| A-27. | CH$_2$CH(CH$_3$)$_2$ | CH$_3$ |
| A-28. | CH$_2$CH(CH$_3$)$_2$ | CH$_2$CH$_3$ |
| A-29. | (±) CH(CH$_2$CH$_3$)CH$_3$ | H |
| A-30. | (±) CH(CH$_2$CH$_3$)CH$_3$ | CH$_3$ |
| A-31. | (±) CH(CH$_2$CH$_3$)CH$_3$ | CH$_2$CH$_3$ |
| A-32. | (R) CH(CH$_2$CH$_3$)CH$_3$ | H |
| A-33. | (R) CH(CH$_2$CH$_3$)CH$_3$ | CH$_3$ |
| A-34. | (R) CH(CH$_2$CH$_3$)CH$_3$ | CH$_2$CH$_3$ |
| A-35. | (S) CH(CH$_2$CH$_3$)CH$_3$ | H |
| A-36. | (S) CH(CH$_2$CH$_3$)CH$_3$ | CH$_3$ |
| A-37. | (S) CH(CH$_2$CH$_3$)CH$_3$ | CH$_2$CH$_3$ |
| A-38. | (±) CH(CH$_3$)—CH(CH$_3$)$_2$ | H |
| A-39. | (±) CH(CH$_3$)—CH(CH$_3$)$_2$ | CH$_3$ |
| A-40. | (±) CH(CH$_3$)—CH(CH$_3$)$_2$ | CH$_2$CH$_3$ |
| A-41. | (R) CH(CH$_3$)—CH(CH$_3$)$_2$ | H |
| A-42. | (R) CH(CH$_3$)—CH(CH$_3$)$_2$ | CH$_3$ |
| A-43. | (R) CH(CH$_3$)—CH(CH$_3$)$_2$ | CH$_2$CH$_3$ |
| A-44. | (S) CH(CH$_3$)—CH(CH$_3$)$_2$ | H |
| A-45. | (S) CH(CH$_3$)—CH(CH$_3$)$_2$ | CH$_3$ |
| A-46. | (S) CH(CH$_3$)—CH(CH$_3$)$_2$ | CH$_2$CH$_3$ |
| A-47. | (±) CH(CH$_3$)—C(CH$_3$)$_3$ | H |
| A-48. | (±) CH(CH$_3$)—C(CH$_3$)$_3$ | CH$_3$ |
| A-49. | (±) CH(CH$_3$)—C(CH$_3$)$_3$ | CH$_2$CH$_3$ |
| A-50. | (R) CH(CH$_3$)—C(CH$_3$)$_3$ | H |
| A-51. | (R) CH(CH$_3$)—C(CH$_3$)$_3$ | CH$_3$ |
| A-52. | (R) CH(CH$_3$)—C(CH$_3$)$_3$ | CH$_2$CH$_3$ |
| A-53. | (S) CH(CH$_3$)—C(CH$_3$)$_3$ | H |
| A-54. | (S) CH(CH$_3$)—C(CH$_3$)$_3$ | CH$_3$ |
| A-55. | (S) CH(CH$_3$)—C(CH$_3$)$_3$ | CH$_2$CH$_3$ |
| A-56. | (±) CH(CH$_3$)—CF$_3$ | H |
| A-57. | (±) CH(CH$_3$)—CF$_3$ | CH$_3$ |
| A-58. | (±) CH(CH$_3$)—CF$_3$ | CH$_2$CH$_3$ |
| A-59. | (R) CH(CH$_3$)—CF$_3$ | H |
| A-60. | (R) CH(CH$_3$)—CF$_3$ | CH$_3$ |
| A-61. | (R) CH(CH$_3$)—CF$_3$ | CH$_2$CH$_3$ |
| A-62. | (S) CH(CH$_3$)—CF$_3$ | H |
| A-63. | (S) CH(CH$_3$)—CF$_3$ | CH$_3$ |
| A-64. | (S) CH(CH$_3$)—CF$_3$ | CH$_2$CH$_3$ |
| A-65. | (±) CH(CH$_3$)—CCl$_3$ | H |
| A-66. | (±) CH(CH$_3$)—CCl$_3$ | CH$_3$ |
| A-67. | (±) CH(CH$_3$)—CCl$_3$ | CH$_2$CH$_3$ |
| A-68. | (R) CH(CH$_3$)—CCl$_3$ | H |
| A-69. | (R) CH(CH$_3$)—CCl$_3$ | CH$_3$ |
| A-70. | (R) CH(CH$_3$)—CCl$_3$ | CH$_2$CH$_3$ |
| A-71. | (S) CH(CH$_3$)—CCl$_3$ | H |
| A-72. | (S) CH(CH$_3$)—CCl$_3$ | CH$_3$ |
| A-73. | (S) CH(CH$_3$)—CCl$_3$ | CH$_2$CH$_3$ |
| A-74. | CH$_2$C(CH$_3$)=CH$_2$ | H |
| A-75. | CH$_2$C(CH$_3$)=CH$_2$ | CH$_3$ |
| A-76. | CH$_2$C(CH$_3$)=CH$_2$ | CH$_2$CH$_3$ |
| A-77. | Cyclopentyl | H |
| A-78. | Cyclopentyl | CH$_3$ |
| A-79. | Cyclopentyl | CH$_2$CH$_3$ |
| A-80. | Cyclohexyl | H |
| A-81. | Cyclohexyl | CH$_3$ |
| A-82. | Cyclohexyl | CH$_2$CH$_3$ |
| A-83. | —(CH$_2$)$_4$— | |
| A-84. | (±) —(CH$_2$)$_2$—CH(CH$_3$)—CH$_2$— | |
| A-85. | (R) —(CH$_2$)$_2$—CH(CH$_3$)—CH$_2$— | |
| A-86. | (S) —(CH$_2$)$_2$—CH(CH$_3$)—CH$_2$— | |
| A-87. | —(CH$_2$)$_2$—CH(OCH$_3$)—CH$_2$— | |
| A-88. | —(CH$_2$)$_2$—CH(CH$_2$CH$_3$)—CH$_2$— | |
| A-89. | —(CH$_2$)$_2$—CH[CH(CH$_3$)$_2$]—CH$_2$— | |
| A-90. | (±) —(CH$_2$)$_3$—CH(CH$_3$)— | |
| A-91. | (±) —CH(CH$_3$)—(CH$_2$)$_2$—CH(CH$_3$)— | |
| A-92. | —CH$_2$—CH=CH—CH$_2$— | |
| A-93. | —(CH$_2$)$_5$— | |
| A-94. | (±) —(CH$_2$)$_4$—CH(CH$_3$)— | |
| A-95. | —(CH$_2$)$_2$—CH(CH$_3$)—(CH$_2$)$_2$— | |
| A-96. | (±) —(CH$_2$)$_3$—CH(CH$_3$)—CH$_2$— | |
| A-97. | (R) —(CH$_2$)$_3$—CH(CH$_3$)—CH$_2$— | |
| A-98. | (S) —(CH$_2$)$_3$—CH(CH$_3$)—CH$_2$— | |
| A-99. | —(CH$_2$)$_2$—C(O[CH$_2$]$_2$O)—(CH$_2$)$_2$— | |

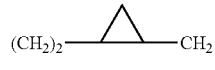

A-100.   (CH$_2$)$_2$—△—CH$_2$

| A-101. | —(CH$_2$)$_2$—C(O[CH$_2$]$_3$O)—(CH$_2$)$_2$— |
| A-102. | —(CH$_2$)$_2$—CH=CH—CH$_2$— |

The compounds I are suitable as fungicides. They are distinguished by an outstanding effectiveness against a broad spectrum of phytopathogenic fungi, especially from the classes of the Ascomycetes, Deuteromycetes, Oomycetes and Basidiomycetes. Some are systemically effective and they can be used in plant protection as foliar and soil fungicides.

They are particularly important in the control of a multitude of fungi on various cultivated plants, such as wheat, rye, barley, oats, rice, corn, grass, bananas, cotton, soy-bean, coffee, sugar cane, vines, fruits and ornamental plants, and vegetables, such as cucumbers, beans, tomatoes, potatoes and cucurbits, and on the seeds of these plants.

They are especially suitable for controlling the following plant diseases:

*Alternaria* species on fruit and vegetables,
*Bipolaris* and *Drechslera* species on cereals, rice and lawns,
*Blumeria graminis* (powdery mildew) on cereals,
*Botrytis cinerea* (gray mold) on strawberries, vegetables, ornamental plants and grapevines,
*Erysiphe cichoracearum* and *Sphaerotheca fuliginea* on cucurbits,
*Fusarium* and *Verticillium* species on various plants,
*Mycosphaerella* species on cereals, bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
*Pseudoperonospora* species on hops and cucumbers,
*Puccinia* species on cereals,
*Pyricularia oryzae* on rice,
*Rhizoctonia* species on cotton, rice and lawns,
*Septoria tritici* and *Stagonospora nodorum* on wheat,
*Uncinula necator* on grapevines,
*Ustilago* species on cereals and sugar cane, and
*Venturia* species (scab) on apples and pears.

The compounds I are also suitable for controlling harmful fungi, such as *Paecilomyces variotii*, in the protection of materials (for example wood, paper, paint dispersions, fibers or fabrics) and in the protection of stored products.

The compounds I are employed by treating the fungi or the plants, seeds, materials or soil to be protected from fungal attack with a fungicidally effective amount of the active compounds. The application can be carried out both before and after the infection of the materials, plants or seeds by the fungi.

The fungicidal compositions generally comprise between 0.1 and 95%, preferably between 0.5 and 90%, by weight of active compound.

When employed in plant protection, the amounts applied are, depending on the kind of effect desired, between 0.01 and 2.0 kg of active compound per ha.

In seed treatment, amounts of active compound of 0.001 to 0.1 g, preferably 0.01 to 0.05 g, per kilogram of seed are generally necessary.

When used in the protection of materials or stored products, the amount of active compound applied depends on the kind of application area and on the desired effect. Amounts customarily applied in the protection of materials are, for example, 0.001 g to 2 kg, preferably 0.005 g to 1 kg, of active compound per cubic meter of treated material.

The compounds I can be converted to the customary formulations, for example solutions, emulsions, suspensions, dusts, powders, pastes and granules. The application form depends on the particular intended use; it should in any case ensure a fine and uniform distribution of the compound according to the invention.

The formulations are prepared in a known manner, for example by extending the active compound with solvents and/or carriers, if desired using emulsifiers and dispersants. Solvents/auxiliaries which are suitable are essentially:

water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

carriers such as ground natural minerals (for example kaolins, clays, talc, chalk) and ground synthetic minerals (for example highly disperse silica, silicates);

emulsifiers such as nonionic and anionic emulsifiers (for example polyoxyethylene fatty alcohol ethers, alkylsulfonates and arylsulfonates) and dispersants such as lignosulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compounds. The active compounds are employed in a purity of from 90% to 100%, preferably 95% to 100% (according to NMR spectrum).

The following are examples of formulations: 1. Products for dilution with water

A) Water-soluble Concentrates (SL)

10 parts by weight of a compound according to the invention are dissolved in water or in a water-soluble solvent. As an alternative, wetters or other auxiliaries are added. The active compound dissolves upon dilution with water.

B) Dispersible Concentrates (DC)

20 parts by weight of a compound according to the invention are dissolved in cyclohexanone with addition of a dispersant, for example polyvinylpyrrolidone. Dilution with water gives a dispersion.

C) Emulsifiable Concentrates (EC)

15 parts by weight of a compound according to the invention are dissolved in xylene with addition of calcium dodecylbenzenesulfonate and castor oil ethoxylate (in each case 5% strength). Dilution with water gives an emulsion.

D) Emulsions (EW, EO)

40 parts by weight of a compound according to the invention are dissolved in xlene with addition of calcium dodecylbenzenesulfonate and castor oil ethoxylate (in each case 5% strength). This mixture is introduced into water by means of an emulsifier (Ultratursax) and made into a homogeneous emulsion. Dilution with water gives an emulsion.

E) Suspensions (SC, OD)

In an agitated ball mill, 20 parts by weight of a compound according to the invention are comminuted with addition of dispersants, wetters and water or an organic solvent to give a fine active compound suspension. Dilution with water gives a stable suspension of the active compound.

F) Water-dispersible Granules and Water-soluble Granules (WG, SG)

50 parts by weight of a compound according to the invention are ground finely with addition of dispersants and wetters and made into water-dispersible or water-soluble granules by means of technical appliances (for example extrusion, spray tower, fluidized bed). Dilution with water gives a stable dispersion or solution of the active compound.

G) Water-Dispersible Powders and Water-Soluble Powders (WP, SP)

75 parts by weight of a compound according to the invention are ground in a rotor-stator mill with addition of dispersants, wetters and silica gel. Dilution with water gives a stable dispersion or solution of the active compound.

2. Products to be Applied Undiluted

H) Dusts (DP)

5 parts by weight of a compound according to the invention are ground finely and mixed intimately with 95% of finely divided kaolin. This gives a dustable product.

I) Granules (GR, FG, GG, MG)

0.5 part by weight of a compound according to the invention is ground finely and associated with 95.5% carriers. Customary methods are extrusion, spray-drying or the fluidized bed. This gives granules to be applied undiluted.

J) ULV Solutions (UL)

10 parts by weight of a compound according to the invention are dissolved in an organic solvent, for example xylene. This gives a product to be applied undiluted.

The active compounds can be used as such, in the form of their formulations or of the application forms prepared therefrom, e.g. in the form of directly sprayable solutions, powders, suspensions or dispersions, emulsions, oil dispersions, pastes, dustable products, preparations for broadcasting or granules, by spraying, atomizing, dusting, broadcasting or watering. The application forms depend entirely on the intended uses; they should always ensure the finest possible dispersion of the active compounds according to the invention.

Aqueous application forms can be prepared from emulsifiable concentrates, pastes or wettable powders (spray powders, oil dispersions) by addition of water. To prepare emulsions, pastes or oil dispersions, the substances can be homogenized in water, as such or dissolved in an oil or solvent, by means of wetting agents, tackifiers, dispersants or emulsifiers. However, it is also possible to prepare concentrates comprising active substance, wetting agent, tackifier, dispersant or emulsifier and possibly solvent or oil which are suitable for dilution with water.

The concentrations of active compound in the ready-for-use preparations can be varied within relatively wide ranges. In general, they are between 0.0001 and 10%, preferably between 0.01 and 1%.

The active compounds can also be used with great success in the ultra-low volume (ULV) process, it being possible to apply formulations with more than 95% by weight of active compound or even the active compound without additives.

Oils of various types, wetting agents, adjuvants, herbicides, fungicides, other pesticides and bactericides can be added to the active compounds, if need be also not until immediately before use (tank mix). These agents can be added to the preparations according to the invention in a weight ratio of 1:10 to 10:1.

The preparations according to the invention can, in the application form as fungicides, also be present together with other active compounds, e.g. with herbicides, insecticides, growth regulators, fungicides or also with fertilizers. On mixing the compounds I or the preparations comprising them in the application form as fungicides with other fungicides, in many cases an expansion of the fungicidal spectrum of activity is obtained.

The following list of fungicides, with which the compounds according to the invention can be used in conjunction, is intended to illustrate the possible combinations but does not limit them:

acylalanines, such as benalaxyl, metalaxyl, ofurace or oxadixyl, amine derivatives, such as aldimorph, dodine, dodemorph, fenpropimorph, fenpropidin, guazatine, iminoctadine, spiroxamine or tridemorph, anilinopyrimidine, such as pyrimethanil, mepanipyrim or cyprodinyl, antibiotics, such as cycloheximide, griseofulvin, kasugamycin, natamycin, polyoxin or streptomycin, azoles, such as bitertanol, bromoconazole, cyproconazole, difenoconazole, dinitroconazole, epoxiconazole, fenbuconazole, fluquinconazole, flusilazole, flutriafol, hexaconazole, imazalil, metconazole, myclobutanil, penconazole, propiconazole, prochloraz, prothioconazole, tebuconazole, triadimefon, triadimenol, triflumizole or triticonazole, dicarboximides, such as iprodione, myclozolin, procymidone or vinclozolin, dithiocarbamates, such as ferbam, nabam, maneb, mancozeb, metam, metiram, propineb, polycarbamate, thiram, ziram or zineb, heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophanate-methyl, tiadinil, tricyclazole or triforine, copper fungicides, such as Bordeaux mixture, copper acetate, copper oxychloride or basic copper sulfate, nitrophenyl derivatives, such as binapacryl, dinocap, dinobuton or nitrophthal-isopropyl, phenylpyrroles, such as fenpiclonil or fludioxonil, sulfur, other fungicides, such as acibenzolar-S-methyl, benthiavalicarb, carpropamid, chlorothalonil, cyflufenamid, cymoxanil, dazomet, diclomezine, diclocymet, diethofencarb, edifenphos, ethaboxam, fenhexamid, fentin acetate, fenoxanil, ferimzone, fluazinam, fosetyl, fosetyl-aluminum, iprovalicarb, hexachlorobenzene, metrafenone, pencycuron, propamocarb, phthalide, toiclofos-methyl, quintozene or zoxamide, strobilurins, such as azoxystrobin, dimoxystrobin, fluoxastrobin, kresoxim-methyl, metominostrobin, orysastrobin, picoxystrobin, pyraclostrobin or trifloxystrobin, sulfenic acid derivatives, such as captafol, captan, dichlofluanid, folpet or tolylfluanid, cinnamides and analogous compounds, such as dimethomorph, flumetover or flumorph.

SYNTHESIS EXAMPLES

Example 1

Synthesis of (S)-4-chloro-6-(2,2,2-trifluoro-1-methylethylamino)-5-(2,4,6-trifluorophenyl)pyrimidine-2-thiocarbamide

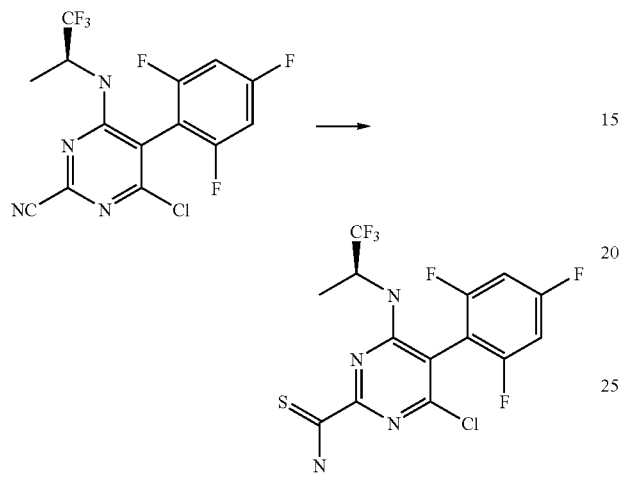

At room temperature, hydrogen sulfide was introduced for 5 minutes into a solution of 0.5 g (1.35 mmol) of (S)-4-chloro-6-(2,2,2-trifluoro-1-methylethylamino)-5-(2,4,6-trifluorophenyl)pyrimidine-2-carbonitrile, prepared according to WO 03/043993, in 0.16 g of triethylamine and 6 ml of N-methylpyrrolidone. After the reaction had ended, 20 ml of water were added, the mixture was neutralized with acetic acid and extracted with methyl tert-butyl ether and the organic phase was washed with water, dried over magnesium sulfate and concentrated.

Yield: 0.44 g (81% of theory) M.p.: 101-103° C.

Example 2

Synthesis of 4-sec-butylamino-6-chloro-5-(2-chloro-6-fluorophenyl)-pyrimidine-2-thiocarbamide

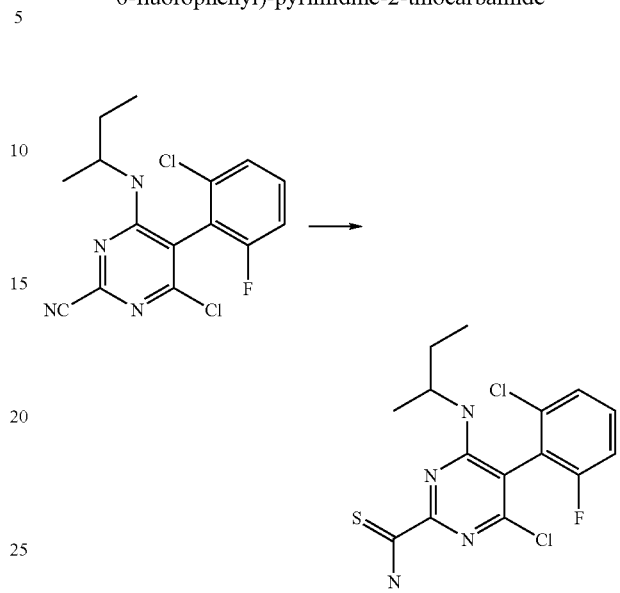

At room temperature, hydrogen sulfide was introduced for 5 minutes into a solution of 1.0 g (2.9 mmol) of 4-sec-butylamino-6-chloro-5-(2-chloro-6-fluorophenyl)pyrimidine-2-carbonitrile in 0.36 g of triethylamine and 12 ml of N-methylpyrrolidone. After the reaction had ended, 20 ml of water were added, the mixture was neutralized with acetic acid and extracted with methyl tert-butyl ether and the organic phase was washed with water, dried over magnesium sulfate and concentrated.

Yield: 0.57 g (53% of theory) M.p.: 147-150° C.

The compounds listed in the table below were synthesized analogously to the procedures given above.

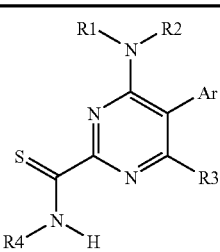

| No. | $R^1$ | $R^2$ | $R^3$ | $R^4$ | Ar | m.p.: [° C.] | $^1$H-NMR [ppm, CHCl$_3$] |
|---|---|---|---|---|---|---|---|
| I-1 | CH$_2$CH$_2$CH(CH$_3$) | CH$_2$CH$_3$ | Cl | H | 2-chloro-6-fluorophenyl | 170-172 | |
| I-2 | (S)-CH(CH$_3$)CF$_3$ | H | Cl | H | 2,4,6-trifluorophenyl | 101-103 | |
| I-3 | CH(CH$_3$)$_2$ | H | Cl | H | 2-chloro-6-fluorophenyl | | 1.21 (d, 6H); 4.42 (m, br, 2H); 7.21 (t, 1H); 7.36 (m, 2H); 8.03 (s, br, 1H); 9.12 (s, br, 1H) |
| I-4 | CH(CH$_3$)$_2$ | H | Cl | H | 2,4,6-trifluorophenyl | 145-149 | |
| I-5 | CH(CH$_3$)CH$_2$CH$_3$ | H | Cl | H | 2,4,6-trifluorophenyl | 110-113 | |
| I-6 | CH$_2$CH$_2$CH$_2$CH | | Cl | H | 2,4,6-trifluorophenyl | | 1.27 (d, 3H); 1.6 (m, 4H); 3.92 (m, 2H); 4.48 (m, 1H); 6.76 (m, 2H); 7.80 (s, br, 1H); 9.04 (s, br, 1H) |
| I-7 | CH$_2$C(CH$_3$)=CH$_2$ | CH$_2$CH$_3$ | Cl | H | 2,4,6-trifluorophenyl | 130-132 | |
| I-8 | CH(CH$_3$)CH$_2$CH$_3$ | H | Cl | H | 2-chloro-6-fluorophenyl | 147-150 | |

-continued

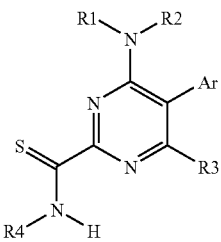

| No. | R¹ | R² | R³ | R⁴ | Ar | m.p.: [° C.] | ¹H-NMR [ppm, CHCl₃] |
|---|---|---|---|---|---|---|---|
| I-9 | CH₂C(CH₃)=CH₂ | CH₂CH₃ | Cl | H | 2-chloro-6-fluorophenyl | | 1.03 (m, 3H); 1.45 (s, 3H); 3.24 (m, 1H); 3.50 (m, 1H); 3.83 (m, 2H); 4.79 (s, 2H); 7.10 (m, 1H); 7.36 (m, 2H); 8.00 (s, br, 1H); 9.05 (s, br, 1H) |
| I-10 | (S)-CH(CH₃)CH(CH₃)₂ | H | Cl | H | 2-chloro-6-fluorophenyl | | 0.88 (dd, 6H); 1.20 (dd, 3H); 1.79 (m, 1H); 4.45 (m, br, 2H); 7.20 (m, 1H); 7.43 (m, 2H); 7.70 (s, br, 1H); 9.06 (s, br, 1H) |
| I-11 | (S)-CH(CH₃)CH(CH₃)₂ | H | Cl | H | 2-chloro-4-fluorophenyl | | 0.85 (dd, 6H); 1.15 (dd, 3H); 1.75 (m, 1H); 4.40 (m, br, 2H); 7.19 (m, 1H); 7.33 (m, 2H); 8.03 (s, br, 1H); 9.11 (s, br, 1H) |
| I-12 | (S)-CH(CH₃)CH(CH₃)₂ | H | | | 2,4-difluorophenyl | | 0.84 (dd, 6H); 1.16 (dd, 3H); 1.78 (m, 1H); 4.30 (m, br, 2H); 7.00 (m, 1H); 7.08 (m, 1H); 7.38 (m, 1H); 8.0 (s, br, 1H); 9.0 (s, br, 1H) |
| I-13 | CH₂CH=CH₂ | CH₂CH=CH₂ | Cl | H | 2,4,6-trifluorophenyl | 54-60 | |
| I-14 | (S)-CH(CH₃)CH(CH₃)₂ | | Cl | H | 2-chloro-6-fluorophenyl | 120-123 | |
| I-15 | (S)-CH(CH₃)CH(CH₃)₂ | H | Cl | H | 2,4,6-trifluorophenyl | 142-145 | |
| I-16 | CH₂CH₂CH(CH₃)CH₂CH₂ | | Cl | H | 2,4,6-trifluorphenyl | 66-69 | |
| I-17 | (S)-CH(CH₃)CF₃ | H | Cl | COCH₃ | 2,4,6-trifluorophenyl | 55-58 | |
| I-18 | (S)-CH(CH₃)CF₃ | H | Cl | H | 2-chloro-4-fluorophenyl | | 1.34 (m, 3H), 4.4 (d, 1H); 4.94 (m, 1H); 7.19 (m, 1H); 7.31 (m, 2H); 8.31 (s, 1H); 8.92 (s, 1H); 11.61 (s, 1H) |
| I-19 | CH₂CH₃ | CH₂CH₃ | Cl | H | 2,4,6-trifluorophenyl | 55-58 | 1.03 (m, 6H); 3.37 (m, 4H); 6.8 (m, 2H); 8.03 (m, 1H); 9.02 (m, 1H) |
| I-20 | (S)-CH(CH₃)CH(CH₃)₂ | H | Cl | H | 2-chloro-4-fluorophenyl | | 0.85 (m, 6H); 1.1 (m, 3H); 1.7 (m, 1H); 4.03 (s, 1H); 4.35 (d, 1H); 7.17 (m, 1H); 7.33 (m, 2H); 7.7 (s, 1H); 8.86 (s, 1H); 11.39 (s, 1H) |
| I-21 | CH₂CH₃ | CH₂CH₃ | Cl | COCH₃ | 2,4,6-trifluorophenyl | | 1.07 (m, 6H); 2.65 (s, 3H); 3.37 (m, 4H); 6.83 (t, 2H); 11.62 (s, 1H) |
| I-22 | CH(CH₃)CH₂CH₃ | H | Cl | H | 2-chloro-4-fluorophenyl | 172-175 | |
| I-23 | CH(CH₃)₂ | H | Me | H | 2,4,6-trifluorophenyl | 158 | |
| I-24 | CH(CH₃)CH₂CH₃ | H | Me | H | 2,4,6-trifluorophenyl | 114-117 | |
| I-25 | CH₂CH₂CH(CH₃)CH₂CH₂ | | Me | H | 2,4,6-trifluorophenyl | 149-151 | |

Examples of the Action Against Harmful Fungi

The fungicidal action of the compounds of the formula I was demonstrated by the following experiments:

The active compounds were prepared separately as a stock solution with 0.25% by weight of active compound in acetone or DMSO. 1% by weight of the emulsifier Uniperol® EL (wetting agent having emulsifying and dispersing action based on ethoxylated alkyl-phenols) was added to this solution. The stock solutions of the active compounds were diluted with water to the desired concentration.

Use Examples

1) Activity Against Gray Mold on Bell Pepper Leaves Caused by Botrytis cinerea, Protective Application Bell pepper seedlings of the cultivar "Neusiedler Ideal Elite" were, after 4-5 leaves were well developed, sprayed to runoff point with an aqueous suspension having a concentration of active compound of 250 ppm. The next day, the treated plants were inoculated with a spore suspension of Botrytis cinerea, this contained 1.7×10⁶ spores/ml in a 2% strength aqueous biomalt solution. The test plants were then placed in a climate-chamber at 22-24° C. and high atmospheric humidity. After 5 days, the extent of the fungal infection on the leaves was determined visually in %.

In this test, the plants which had been treated with compounds I-2, I-3, I-4, I-6, I-7, I-8, I-10 and I-11 were not infected, whereas the untreated plants were 90% infected.

2) Activity Against Mildew on Cucumber Leaves Caused by Sphaerotheca fuliginea, Protective Application The leaves of potted cucumber seedlings of the cultivar "Chinese snake" were, at the cutyledon stage, sprayed to runoff point with an aqueous suspension having a concentration of active compound of 250 ppm. 20 hours after the spray coating had dried, the plants were inoculated with an aqueous spore suspension of mildew of cucumber (Sphaerotheca fuliginea). The plants were then cultivated in a greenhouse at 20-24° C. and 60-80% relative atmospheric humidity for 7 days. The extent of the mildew development was then determined visually in % infection of the cotyledon area.

In this test, the plants which had been treated with compounds I-2, I-3, I-4, I-5, I-6, I-7, I-8, I-9, I-10 and I-11 showed no infection or infection of less than 10%, whereas the untreated plants were 100% infected.

3) Activity Against Early Blight of Tomatoes Caused by *Altemaria solani*

Leaves of potted plants of the cultivar "Goldene Prinzessin" were sprayed to runoff point with an aqueous suspension having an active compound concentration of 250 ppm. The next day, the leaves were infected with an aqueous spore suspension of *Altemaria solani* in a 2% biomalt solution having a density of $0.17 \times 10^6$ spores/ml. The plants were then placed in a water-vapor-saturated chamber at 20-22° C. After 5 days, the early blight on the untreated, but infected control plants had developed to such an extent that the infection could be determined visually in %.

In this test, the plants which had been treated with compounds I-13, I-14, I-15, I-16, I-17 and I-19 had an infection of <5%, while the untreated plants were 80% infected.

4) Activity Against Net Blotch of Barley Caused by *Pyrenophora teres*

Leaves of pot-grown barley seedlings of the cultivar "Hanna" were sprayed to runoff point with an aqueous suspension having an active compound concentration of 250 ppm. 24 hours after the spray coating had dried on, the test plants were inoculated with an aqueous suspension of spores of *Pyrenophora* [syn. *Drechslera*] *teres*, the causative agent of net blotch. The test plants were subsequently placed in a greenhouse at temperatures of between 20 and 24° C. and a relative atmospheric humidity of 95 to 100%. After 6 days, the extent of development of the disease was determined visually in % of infection of the total leaf area.

In this test, the plants treated with compounds I-13, I-14, I-15, I-16, I-17 and I-19 had an infection of 10%, while the untreated plants were 80% infected.

What is claimed is:

1. A 2-substituted pyrimidine of the formula I

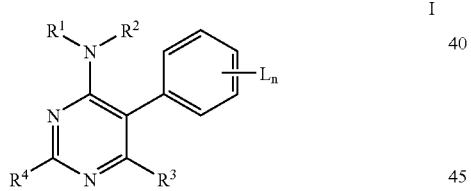

I in which the index and the substituents are as defined below:

n is an integer from 1 to 5;

L is halogen, cyano, cyanato (OCN), $C_1$-$C_8$-alkyl, $C_2$-$C_8$-alkenyl, $C_2$-$C_8$-alkynyl, $C_1$-$C_6$-alkoxy, $C_2$-$C_8$-alkyenyloxy, $C_2$-$C_8$-alkynyloxy, $C_3$-$C_6$-cycloalkyl, $C_4$-$C_6$-cycloalkenyl, $C_3$-$C_6$-cycloalkyloxy, $C_4$-$C_6$-cycloalkenyloxy, nitro, —C(=O)-A, —C(=O)—O-A, —C(=O)—N(A')A, C(A')(=N—OA), N(A')A, N(A')—C(=O)-A, N(A")—C(=O)—N(A')A, $S(=O)_m$-A, $S(=O)_m$—O-A or $S(=O)_m$—N(A')A, m is 0, 1 or 2;

A, A', A" independently of one another are hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, phenyl, where the organic radicals may be partially or fully halogenated or may be substituted by nitro, cyanato, cyano or $C_1$-$C_4$-alkoxy; or A and A' together with the atoms to which they are attached are a five- or six-membered saturated, partially unsaturated or aromatic heterocycle which contains one to four heteroatoms from the group consisting of O, N and S;

where the aliphatic groups of the radical definitions of L for their part may be partially or fully halogenated or may carry one to four groups $R^u$:

$R^u$ is cyano, $C_1$-$C_6$-alkoxy, $C_3$-$C_6$-cycloalkyl, $C_2$-$C_8$-alkenyloxy, $C_2$-$C_8$-alkynyloxy, $C_4$-$C_6$-cycloalkenyl, $C_3$-$C_6$-cycloalkyloxy, $C_4$-$C_6$-cycloalkenyloxy, —C(=O)-A, —C(=O)—O-A, —C(=O)—N(A')A, C(A')(=N—OA), N(A')A, N(A')-C(=O)-A, N(A")-C(=O)—N(A')A, $S(=O)_m$-A, $S(=O)_m$—O-A or $S(=O)_m$—N(A')A;

$R^1$, $R^2$ independently of one another are $C_1$-$C_6$-alkyl, $C_2$-$C_6$-alkenyl, $C_2$-$C_6$-alkynyl, $C_3$-$C_6$-cycloalkyl, $C_3$-$C_6$-halocycloalkyl, where the aliphatic groups of the radical definitions of $R^1$ and $R^2$ may for their part be partially or fully halogenated or may carry one to four groups $R^v$:

$R^v$ is cyano, $C_3$-$C_6$-cycloalkyl, $C_4$-$C_6$-cycloalkenyl, hydroxyl, $C_1$-$C_6$-alkoxy, $C_2$-$C_8$-alkenyloxy, $C_2$-$C_8$-alkynyloxy, $C_3$-$C_6$-cycloalkyloxy, $C_4$-$C_6$-cycloalkenyloxy, $C_1$-$C_6$-alkylthio, —C(=O)-A, —C(=O)—O-A, —C(=O)—N(A')A, C(A')(=N—OA), N(A')A, N(A')—C(=O)-A, N(A")—C(=O)—N(A')A, $S(=O)_m$-A, $S(=O)_m$—O-A or $S(=O)_m$—N(A')A or phenyl, where the phenyl moiety may carry one to three radicals selected from the group consisting of halogen, $C_1$-$C_6$-alkyl, $C_2$-$C_6$-alkenyl, $C_2$-$C_6$-alkynyl, $C_3$-$C_6$-cycloalkyl, $C_1$-$C_6$-halogenalkyl, $C_1$-$C_6$-alkoxy, cyano, nitro, —C(=O)-A, —C(=O)—O-A, —C(=O)—N(A')A, C(A')(=N—OA), N(A')A;

$R^2$ may additionally be hydrogen;

$R^1$ and $R^2$ may also, together with the nitrogen atom to which they are attached, form a saturated or unsaturated five- or six-membered ring which may be interrupted by an ether (—O—), carbonyl (C=O—), thio (—S—), sulfoxyl (—S[=O]—) or sulfenyl (—SO$_2$—) or a further amino —(—N($R^a$) group where $R^a$ is hydrogen or $C_1$-$C_6$ alkyl and/or may contain one or more substituents from the group consisting of halogen, $C_1$-$C_6$-alkyl, $C_1$-$C_6$-haloalkyl and oxy-$C_1$-$C_3$-alkylenoxy;

$R^3$ is halogen, cyano, $C_1$-$C_4$-alkyl, $C_2$-$C_4$-alkenyl, $C_2$-$C_4$-alkynyl, $C_3$-$C_6$-cycloalkyl, $C_1$-$C_4$-alkoxy, $C_3$-$C_4$-alkenyloxy, $C_3$-$C_4$-alkynyloxy, $C_1$-$C_6$-alkylthio, di-($C_1$-$C_6$-alkyl)amino or $C_1$-$C_6$-alkylamino, where the alkyl, alkenyl and alkynyl radicals of $R^3$ may be substituted by halogen, cyano, nitro, $C_1$-$C_2$-alkoxy or $C_1$-$C_4$-alkoxycarbonyl;

$R^4$ corresponds to one of the formulae

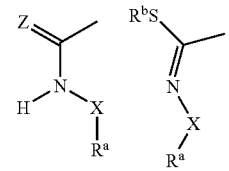

where x is a direct bond, —(C=O)—, —(C=O)—NH, —(C=O)—O—, —O—, —NR$^c$—, where the molecule moiety to the left in each case is attached to the nitrogen atom;

R$^a$ is hydrogen, methyl, benzyl, trifluoromethyl, allyl, propargyl or methoxymethyl;

R$^b$ is hydrogen, C$_1$-C$_6$-alkyl; C$_2$-C$_6$-alkynyl;

R$^c$ is hydrogen, methyl or C$_1$-C$_4$-acyl and

Z is S or NR$^b$;

where the aliphatic groups of the radical definitions of R$^a$, R$^b$ and/or R$^c$ for their part may carry one or two groups R$^w$:

R$^w$ is halogen, OR$^x$, NHR$^x$, C$_1$-C$_6$-alkyl, C$_1$-C$_4$-alkoxycarbonyl, C$_1$-C$_4$-acyl-amino, [1,3]dioxolane-C$_1$-C$_4$-alkyl, [1,3]dioxane-C$_1$-C$_4$-alkyl, where [R$^x$ is hydrogen, methyl, allyl or propargyl.

2. A 2-substituted pyrimidine as claimed in claim 1, where R$^3$ is chlorine, cyano, methyl or methoxy.

3. A 2-substituted pyrimidine as claimed in claim 1, where R$^a$ is hydrogen and R$^b$ is hydrogen, C$_1$-C$_6$-alkyl or C$_2$-C$_6$-alkenyl.

4. A 2-substituted pyrimidine as claimed in claim 1, in which the phenyl group substituted by L$_n$ is the group B

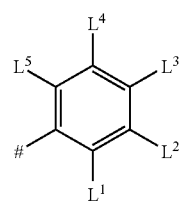

B where # is the point of attachment to the pyrimidine skeleton and

L$^1$ is fluorine, chlorine, CH$_3$ or CF$_3$;

L$^2$, L$^4$ independently of one another are hydrogen, CH$_3$ or fluorine;

L$^3$ is hydrogen, fluorine, chlorine, cyano, CH$_3$, SCH$_3$, OCH$_3$, SO$_2$CH$_3$, NH—C(=O)CH$_3$, N(CH$_3$)—C(=O)CH$_3$ or COOCH$_3$ and L$^5$ is hydrogen, fluorine, chlorine or CH$_3$.

5. A process for preparing 2-substituted pyrimidines of the formula I as claimed in claim 1, where R$^4$ is a thioamide, which comprises reacting a compound of the formula II

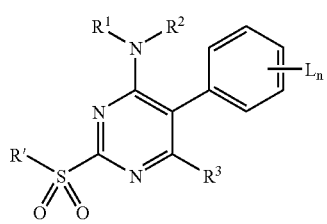

II in which the substituents L, R$^1$, R$^2$ and R$^3$ are as defined in claim 1 and R' is an unsubstituted or substituted C$_1$-C$_6$-alkyl radical or an unsubstituted or substituted phenyl radical with an alkali metal cyanide, alkaline earth metal cyanide or tin cyanide of the formula (III) and then reacting the resulting compound IV

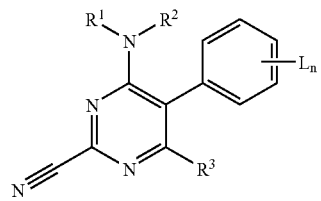

IV with hydrogen sulfide to give IA

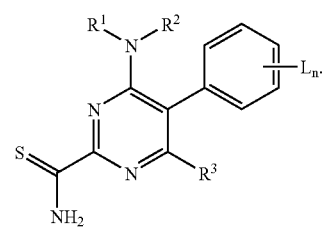

IA

6. A process for preparing compounds of the formula IC, where the substituents L$_n$, R$^1$, R$^2$, R$^3$, R$^a$ and R$^b$ are as defined in claim 1 starting from nitrile IV by reaction with mercaptans of the formula R$^b$SH under acidic conditions and further reaction of the dithiocarboxylic ester of the formula VII which is obtained, with azides of the formula R$^a$N$_3$.

7. A compound of the formula VII

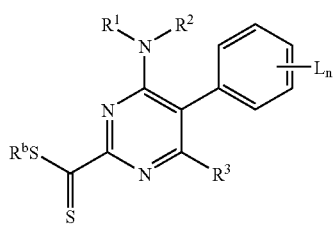

where the substituents $R^1$, $R^2$, $R^3$, $R^b$ and $L_n$ have the meaning in claim 1.

8. A composition suitable for controlling harmful fungi, which composition comprises a solid or liquid carrier and a compound of the formula I as claimed in claim 1.

9. A method for controlling phytopathogenic harmful fungi, which comprises treating the fungi or the materials, plants, the soil or the seeds to be protected against fungal attack with an effective amount of a compound of the formula I as claimed in claim 1.

10. A 2-substituted pyrimidine as claimed in claim 2, in which the phenyl group substituted by $L_n$ is the group B

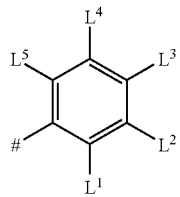

where # is the point of attachment to the pyrimidine skeleton and $L^1$ fluorine, chlorine, $CH_3$ or $CH_3$;

$L^2$, $L^4$ independently of one another are hydrogen, $CH_3$ or fluorine;

$L^3$ is hydrogen, fluorine, chlorine, cyano, $CH_3$, $SCH_3$, $OCH_3$, $SO_2CH_3$, NH—C(=O)$CH_3$, N($CH_3$)—C(=O)$CH_3$ or COO$CH_3$ and $L^5$ is hydrogen, fluorine, chlorine or $CH_3$.

11. A 2-substituted pyrimidine as claimed in claim 3, in which the phenyl group substituted by $L_n$ is the group B

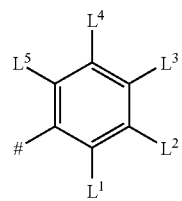

where # is the point of attachment to the pyrimidine skeleton and $L^1$ fluorine, chlorine, $CH_3$ or $CH_3$;

$L^2$, $L^4$ independently of one another are hydrogen, $CH_3$ or fluorine;

$L^3$ is hydrogen, fluorine, chlorine, cyano, $CH_3$, $SCH_3$, $OCH_3$, $SO_2CH_3$, NH—C(=O)$CH_3$, N($CH_3$)—C(=O)$CH_3$ or COO$CH_3$ and $L^5$ is hydrogen, fluorine, chlorine or $CH_3$.

* * * * *